(12) United States Patent
Ringeisen et al.

(10) Patent No.: US 8,389,588 B2
(45) Date of Patent: Mar. 5, 2013

(54) BI-PHASIC COMPRESSED POROUS REINFORCEMENT MATERIALS SUITABLE FOR IMPLANT

(75) Inventors: Timothy A. Ringeisen, Exton, PA (US); Robert L. McDade, Downingtown, PA (US)

(73) Assignee: Kensey Nash Corporation, Exton, PA (US)

( * ) Notice: Subject to any disclaimer, the term of this patent is extended or adjusted under 35 U.S.C. 154(b) by 300 days.

(21) Appl. No.: 12/577,047

(22) Filed: Oct. 9, 2009

(65) Prior Publication Data

US 2010/0278891 A1    Nov. 4, 2010

Related U.S. Application Data

(63) Continuation-in-part of application No. 10/836,740, filed on Apr. 29, 2004, now Pat. No. 7,723,395, and a continuation-in-part of application No. 10/729,146, filed on Dec. 4, 2003, now Pat. No. 8,133,500.

(51) Int. Cl.
*A61F 2/02* (2006.01)

(52) U.S. Cl. ............... 521/50; 521/52; 521/53; 521/82; 623/16.11; 623/17.11; 424/422; 424/423; 424/426

(58) Field of Classification Search .............. 521/50, 521/52, 53, 82; 623/17.11, 16.11; 423/422, 423/423, 426
See application file for complete search history.

(56) References Cited

U.S. PATENT DOCUMENTS

| | | | |
|---|---|---|---|
| 3,616,205 A | 10/1971 | Ito et al. | |
| RE29,487 E | 12/1977 | Gardner, Jr. | |
| 4,283,799 A * | 8/1981 | Pratt et al. | 623/23.37 |
| 4,404,033 A | 9/1983 | Steffan | |
| 4,501,269 A | 2/1985 | Bagby | |
| 4,549,319 A * | 10/1985 | Meyer | 623/23.23 |
| 4,570,271 A | 2/1986 | Sump | |
| 4,660,755 A | 4/1987 | Farling et al. | |
| 4,902,508 A | 2/1990 | Badylak et al. | |
| 4,948,540 A | 8/1990 | Nigam | |
| 4,955,899 A | 9/1990 | Della Corna et al. | |
| 4,969,904 A * | 11/1990 | Koch et al. | 623/23.54 |
| 5,013,324 A | 5/1991 | Zolman et al. | |
| 5,158,574 A | 10/1992 | Stone | |
| 5,206,028 A | 4/1993 | Li | |
| 5,282,861 A | 2/1994 | Kaplan | |
| 5,306,303 A | 4/1994 | Lynch | |
| 5,567,806 A | 10/1996 | Abdul-Malak et al. | |
| 5,571,181 A | 11/1996 | Li | |
| 5,573,784 A | 11/1996 | Badylak et al. | |
| 5,702,449 A | 12/1997 | McKay | |
| 5,891,558 A | 4/1999 | Bell et al. | |
| 5,986,169 A | 11/1999 | Gjunter | |
| 5,997,895 A | 12/1999 | Narotam et al. | |
| 6,039,762 A | 3/2000 | McKay | |
| 6,042,610 A | 3/2000 | Li et al. | |
| 6,241,771 B1 | 6/2001 | Gresser et al. | |
| 6,346,123 B1 | 2/2002 | McKay | |
| 6,371,988 B1 | 4/2002 | Pafford et al. | |
| 6,419,945 B1 | 7/2002 | Gresser et al. | |
| 6,428,579 B1 * | 8/2002 | Valentini | 623/23.76 |
| 6,503,279 B1 | 1/2003 | Webb et al. | |
| 6,548,002 B2 | 4/2003 | Gresser et al. | |
| 6,569,201 B2 | 5/2003 | Moumene et al. | |
| 6,572,619 B2 | 6/2003 | Santilli | |
| 6,599,323 B2 | 7/2003 | Melican et al. | |
| 6,613,091 B1 | 9/2003 | Zdeblick et al. | |
| 6,974,679 B2 | 12/2005 | Andre et al. | |
| 6,974,862 B2 | 12/2005 | Ringeisen et al. | |
| 2002/0127270 A1 | 9/2002 | Li et al. | |

FOREIGN PATENT DOCUMENTS

| | | |
|---|---|---|
| DE | 221358 A1 | 4/1985 |
| EP | 0274898 A2 | 7/1988 |
| EP | 1457214 A1 | 9/2004 |
| EP | 0955024 B1 | 9/2005 |
| FR | 2809313 A1 | 11/2001 |
| WO | WO 90/14055 A1 | 11/1990 |
| WO | WO 99/16381 A1 | 4/1999 |
| WO | WO 03/045460 A1 | 6/2003 |
| WO | WO 2004/062531 A1 | 7/2004 |
| WO | WO 2005/056071 A1 | 6/2005 |

OTHER PUBLICATIONS

Ananthanarayan, V. T. et al., Development of fabric sintering/compaction process . . . , J. Biomaterials Applications, vol. 16, Oct. 2001, 139-148.
Barralet, J. E., et al., Effect of porosity reduction by compaction on compressive strength . . . , J. Biomed. Mater. Res. (Appl. Biomater.) 63: 1-9, 2002.

* cited by examiner

Primary Examiner — Irina S Zemel
(74) Attorney, Agent, or Firm — Jeffrey R. Ramberg

(57) ABSTRACT

A high strength porous biphasic polymeric reinforcement material manufactured by a compression and/or sintering process is disclosed. The material results in a network of interconnected collapsed pores, which forces thin overlapping walls and passages to be created. The network provides permeable access for fluid migration throughout the material. The strength and/or permeability are advantageous for medical devices and implants.

13 Claims, 16 Drawing Sheets

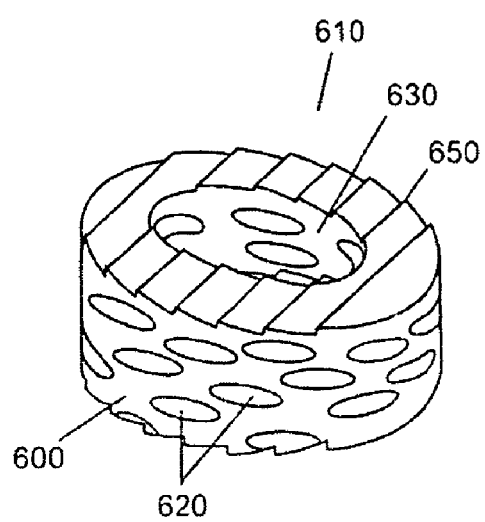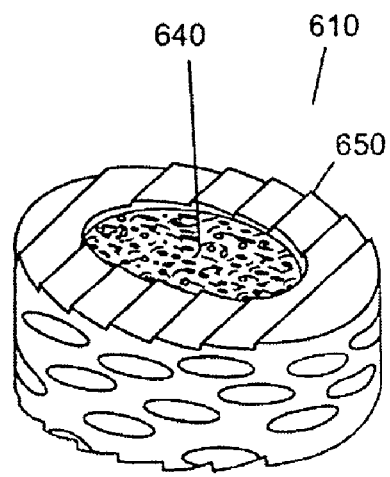
Fig. 6A  Fig. 6B
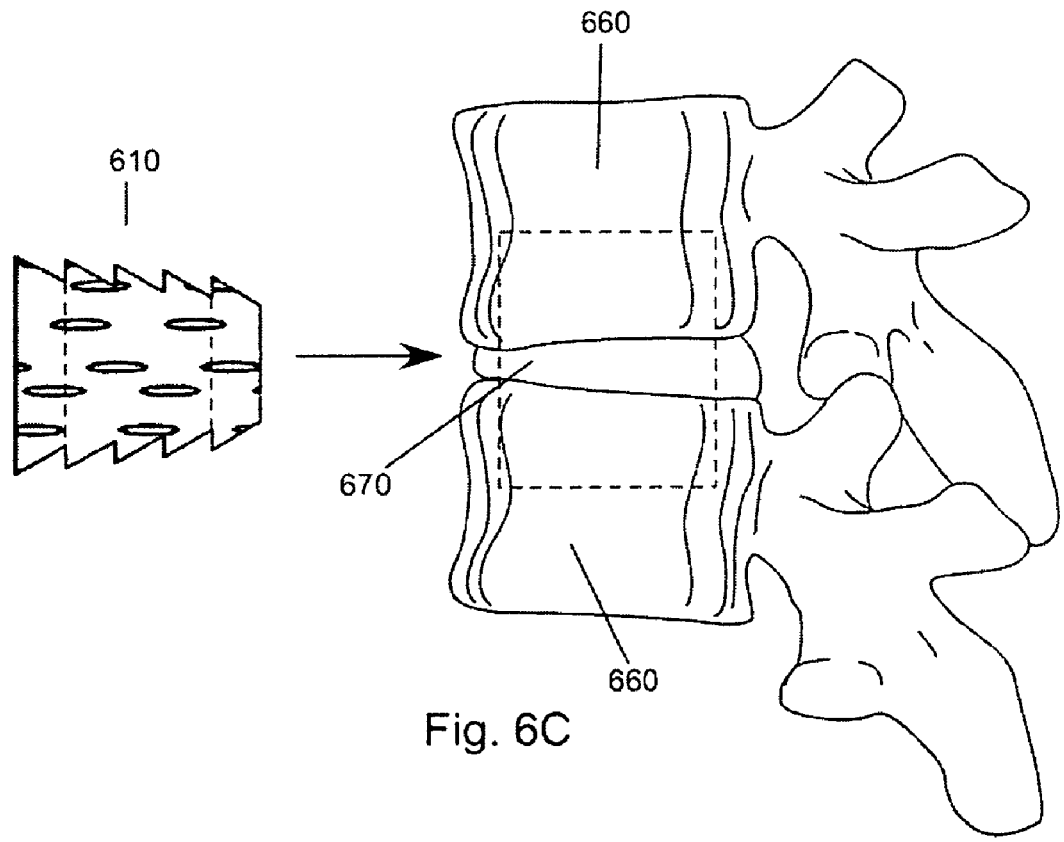
Fig. 6C

BI-PHASIC COMPRESSED POROUS REINFORCEMENT MATERIALS SUITABLE FOR IMPLANT

CROSS-REFERENCE TO RELATED APPLICATIONS

This patent document is a continuation-in-part of U.S. patent application Ser. No. 10/836,740, filed Apr. 29, 2004, now U.S. Pat. No 7,723,395, entitled "Compressed Porous Materials Suitable For Implant". This patent document is also a continuation-in-part of U.S. patent application Ser. No. 10/729,146, filed Dec. 4, 2003, U.S. Pat. No. 8,133,500, entitled "Compressed High Density Fibrous Polymers Suitable for Implant". Both of the above listed applications are assigned to the same assigned as this invention, and whose disclosures are fully incorporated by reference herein.

BACKGROUND OF THE INVENTION

The present invention relates to surgical devices for stabilizing, reinforcing and/or fusing adjacent tissue structures, and, more particularly, to porous and/or partially porous surgical devices for stabilizing, reinforcing and/or fusing the tissues in the fields of bone and soft tissue repair. Generally, this invention concerns internal fixation devices, particularly useful for spinal fusion and hernia repair.

Spinal degenerative diseases (e.g., stenosis, disc disease, spondylosis, etc.), trauma, aging, or a herniated disc can cause compression in the spine thus applying pressure to the nerve roots and/or spinal cord. The compression produces progressive pain, loss of movement and sensation, and sometimes, permanent disability. Spinal fusion is among the standards of care for surgical decompression and stabilization of the spine. Fusion, known also as arthrodesis, is accomplished by the formation of an osseous bridge between adjacent motion segments. The goals of spinal surgery include relieving spinal cord/nerve compression, promoting spinal fusion, increasing stability, maintaining spinal alignment, and restoring disc height. Ideally, reconstructive surgery would result in total spinal fusion with an excellent clinical outcome.

For over 40 years, removal of the problematic disc and fusion of the adjacent vertebrae has been the common treatment for degenerative diseases. The classical surgical procedure is discectomy and interbody fusion with an iliac crest autograft with or without internal fixation. A discectomy typically requires the removal of a portion or the entire intervertebral disc. Different types of grafts (e.g., autograft, allograft, or synthetic ceramics) are used to fill the disc space.

Unfortunately, the use of bone grafts presents several disadvantages. Autogenous bone, which contains matrix molecules and living cells such as osteoblasts that facilitate fusion, is the ideal bone graft; however, postoperative pain is often greater at the harvest site than the surgical site. Additionally, autografts removed from a patient may not yield a sufficient quantity of graft material. Harvesting bone is also associated with high rates of harvest site morbidity and can increase the risk of infection and blood loss. Alternatively, allografts obviate the need for bone harvesting, but have inconsistent mechanical properties. Allografts can also transmit diseases or cause infections, and they have unpredictable and slow fusion rates. Autografts and allografts alone may not provide the stability required to withstand spinal loads and are subject to collapse or failure due to a lack of strength.

In the mid-1970's, Bagby found the clinical results of harvest site morbidity to be unacceptable. In U.S. Pat. No. 4,501,269, he describes the "Bone or Bagby Basket" to eliminate bone graft harvesting and promote bone fusion. Due to the drawbacks of traditional fusion techniques, his initial invention was important and innovative, and it has continually been improved in both design and material selection. These interbody fusion devices are designed to stabilize the vertebral bodies, hold osteogenic material, and promote early stabilization and fusion. The rigidity and structural design of the devices must be able to support the axial loads in the spine. Commercially available spinal interbody fusion devices are made of stainless steel, titanium alloy, carbon fiber, or allograft bone. Often, these devices have void spaces or perforations to allow bone ingrowth.

While carbon fiber and metal interbody fusion devices offer strength advantages, they have several disadvantages. Metal interbody fusion devices are a permanent foreign body and are difficult to remove during revision surgery. Due to the difference in mechanical properties of bone and metal, the main concern of metal interbody fusion devices is stress-shielding, which may cause bone resorption or osteopenia. Although these devices have demonstrated an ability to facilitate fusion, a sufficient fusion is not always achieved between the bone grafts housed within the cage and the vertebral endplates. Achieving a complete bony union in the middle portion of the cage has been particularly problematic. Clinical fusion outcomes may be difficult to assess with metallic interbody fusion devices due to the artifacts and scattering during postoperative CT or MRI scans. Often a complete bony union cannot be seen, making fusion results unreliable. Carbon fiber cages are radiolucent and have properties, such as modulus of elasticity, similar to bone; however, they are also a permanent foreign body. Long-term results with metal and carbon fiber interbody fusion devices are unknown due to the relatively recent development of the implants. Metal cages have been known to fatigue and will eventually fail if a solid bony fusion is not achieved. Over time, metal and carbon fiber cages may migrate or have significant subsidence into the vertebral bodies.

Gjunter (U.S. Pat. No. 5,986,169) describes a porous (i.e., 8 to 90% porosity) material made of a nickel-titanium alloy. The pores form a network of interconnected passageways that permit fluid migration through the material. The material may be used for biomedical implants or non-medical applications. Kaplan (U.S. Pat. No. 5,282,861) and Zdeblick et al. (U.S. Pat. No. 6,613,091) discuss a similar porous material made of a carbon-tantalum composite that could be used to create an implant device. The elasticity of the porous materials is similar to live bony tissue; however, most of the disadvantages associated with carbon fiber and solid metal internal fixation devices still apply to the porous nickel-titanium and carbon-tantalum alloy materials. For example, the porous metal implants remain permanently implanted in the body.

To avoid the disadvantages of metal and carbon fibers devices, bioresorbable materials have been used for years as sutures, bone plates, screws, pins, and other medical devices. A few advantages of bioresorbable implants include biocompatibility, predictable degradation, and complete resorption via natural pathways by the body over a period of time. Polymers are advantageous over other bioresorbable materials, such as ceramics, because they have high toughness and are highly reproducible. The toughness significantly reduces the danger of polymers failing by brittle fracture. Bioresorbable polymers can be formed into spacers, wedges, threaded cages, and a variety of other shapes (e.g., spinal interbody fusion devices).

Bioresorbable implants are transparent to x-rays, and therefore allow, for example, postoperative clinical assessment of a bony union, thereby overcoming one disadvantage of metallic implants. They can perform all the requirements of an interbody cage by providing immediate stability, maintaining foraminal distraction, restoring disc height, and allowing bone ingrowth and fusion. Bioresorbable interbody fusion devices can be produced to provide sufficient strength retention (up to 12 months or longer) in order to allow fusion to occur, then resorb after they are no longer needed. They have the compressive strength to withstand and carry the spinal axial loads; however, they have a modulus of elasticity similar to bone, which limits stress-shielding. Bioresorbable implant devices may feature or contain osteogenic material to attract bone and cells to the implant. Additionally, the bioresorbable devices may be hydrophilic and/or porous. Porous, hydrophilic devices promote the migration of fluid material into the implant, thus allowing a wide variety of tissue ingrowth. The porous bioresorbable implants are fully capable of being replaced by the patient's own bone growth.

Lynch (U.S. Pat. No. 5,306,303), McKay (U.S. Pat. No. 6,346,123) and Webb (U.S. Pat. No. 6,503,279) all describe bioresorbable, porous ceramic materials that may be used in medical implants. McKay and Webb specifically describe an intervertebral fusion device. Due to the brittle nature of ceramic materials, particularly as degradation occurs, the disclosed materials may not withstand the axial loads or cyclic loading of the implant site (e.g., spine) without fracture, collapse, and ultimately device failure.

McKay (U.S. Pat. Nos. 5,702,449 and 6,039,762) describes a spinal cage with an inner core of porous biocompatible material, preferably porous ceramic, which allows tissue ingrowth, and an outer body that can withstand compressive loads. The porous biocompatible material may protrude from the outer shell to permit contact with the vertebral bodies. The implant design with the resorbable inner core does not allow for the use of a bone graft within the device. A high strength outer shell may provide sufficient support; however, it brings concomitant property mismatch with natural bone. Bioceramics as used to form the outer shell are brittle and may fracture under high spinal loads.

Moumene and Serhan (U.S. Pat. No. 6,569,201) disclose a fusion cage with a structural bioresorbable layer disposed upon the outer surface of a non-resorbable support. The purpose of the non-resorbable support is to act as a scaffold for the bioresorbable layer and to hold a bone graft or osteogenic material. The bioresorbable layer would resorb over time, gradually increasing the loading on the bone graft and fusion cage. If the bioresorbable layer and bone graft degrade before fusion can occur, the non-resorbable support may cause stress-shielding. Depending on the thickness of the bioresorbable layer, complete degradation of the layer may cause a great decrease in disc space height. The non-resorbable support will remain a permanent foreign object in the body.

Gresser et al. (U.S. Pat. Nos. 6,241,771 and 6,419,945) describes a spinal interbody fusion device composed of 25-100% bioresorbable material. The device is composed of a resorbable polymer that can produce acidic products upon degradation and includes a neutralization compound to decrease the rate of pH change as the device degrades. In order to withstand the maximum physiologic loading, of at least 10,000 N (the maximum expected lumbar load), the disclosed device must be reinforced with fibers. The device is not porous, consequently limiting bone ingrowth. Similar to metal interbody fusion devices, the device may have void spaces to hold osteogenic materials, such as bone grafts or other osteogenic material. The disclosed device will slowly degrade and lose strength over time with complete resorption predicted to occur by one year. Clinically, complete fusion and bony union may take longer than one year in unstable patients. If fusion of the endplates through the disk space does not occur, the short-term resorption of the device may lead to collapse of the disk space.

Bioresorbable interbody spinal fusion devices offer solutions to disadvantages related to bone grafts and metal and carbon fiber cages. Autografts require bone graft harvesting, which causes postoperative pain and morbidity at the harvest site. Allografts put the patient at risk for infection or transmitted diseases. Metal and carbon fiber cages remain permanent foreign bodies. Metal cages can cause stress-shielding and make fusion assessment difficult. They may also migrate from the implantation site or subside into the vertebral bodies. A need exists for an interbody spinal fusion device that achieves a successful fusion and bony union while avoiding drawbacks associated with the use of metal and carbon fiber devices or bone grafts.

In addition to hard tissue injuries, individuals can sometimes sustain an injury to soft tissue that requires repair by surgical intervention. Such repairs can be effected by suturing the damaged tissue, and/or by mating an implant to the damaged tissue. The implant may provide structural support to the damaged tissue, and it can serve as a substrate upon which cells can grow, thus facilitating more rapid healing.

Herniation is a fairly common tissue injury that usually requires implantation of devices to support and reinforce the tissue weakness. One example is a cystocele, which is a herniation of the bladder. Similar medical conditions include rectoceles (a herniation of the rectum), enteroceles (a protrusion of the intestine through the rectovaginal or vesicovaginal pouch), and enterocystoceles (a double hernia in which both the bladder and intestine protrude). These conditions are usually treated by surgical procedures in which the protruding organs or portions thereof are repositioned. A mesh-like patch is then used to repair the site of the protrusion.

Although these patches are useful to repair some herniations, they are usually not suitable for pelvic floor repair. Moreover, patches or implants that are made from a non-bioabsorbable material can lead to undesirable tissue erosion and abrasion. Other implant materials, which are biologically derived (e.g., allografts and autografts), have disadvantages in that they can contribute to disease transmission, and they are difficult to manufacture in such a way that their properties are reproducible from batch to batch.

Various known devices and techniques for treating such conditions have been described in the prior art. For example, European Patent Application No. 0 955 024 A2 describes a intravaginal set, a medical device used to contract the pelvic floor muscles and elevate the pelvic floor.

In addition, Trip et al (WO 99 16381) describe a biocompatible repair patch having a plurality of apertures formed therein, which is formed of woven, knitted, nonknitted, or braided biocompatable polymers. This patch can be coated with a variety of bioabsorbable materials as well as another material that can decrease the possibility of infection, and/or increase biocompatibility.

Other reinforcing materials are disclosed in U.S. Pat. No. 5,891,558 (Bell et al), U.S. Pat. No. 6,599,323 (Melican et al) and European Patent Application No. 0 274 898 A2 (Hinsch). Bell et al describe biopolymer foams and foam constructs that can be used in tissue repair and reconstruction. Melican and Hinsch both describe an open cell, foam-like implant made from resorbable materials, which has one or more textile reinforcing elements embedded therein. Although potentially useful, the implant material is believed to lack sufficient adaptability and structural integrity to be effectively used as a tissue repair implant.

Despite existing technology, there continues to be a need for a bioabsorbable tissue repair implant having sufficient structural integrity to withstand the stresses associated with implantation into an affected area.

SUMMARY OF THE INVENTION

One embodiment of the invention is a compressed porous matrix material for application to a tissue site in order to support tissue weakness and promote new tissue growth. The invention can take the form of a rigid device with a laminate structure of collapsed pores or a flexible/bendable device in the form of a biphasic sheet. One aspect of this invention is glass transitional deformation or compression of a porous polymeric composition to create a high-strength material that retains the benefits imparted by its porous nature. The compression of the porous composition creates a three-dimensional multi-laminated structure having equivalent mechanical properties to solid (monolithic) polymeric structures without the problems associated with such structures. Compression can affect and create a new structure from the non-compressed porous matrix material. Certain compression methods may create collapsed pore walls that form thin, overlapping laminate walls. Because the laminate walls are formed from thin overlapping laminate walls wherein the walls form a continuous intercommunicating network within the device, the laminate layers are thereby limited in the amount that they can slide, thus eliminating this sliding or delaminating mode of failure, which may otherwise be seen. Depending on the amount of compression, the porous matrix material may have a few collapsed pores or may be completely made up of thin, collapsed pores. Variations in the compression method can create collapsed pores that did not form thin laminate walls, but instead the pores are condensed to a fraction of their original size. Due to pores that collapse or give way first, the pores throughout the material may vary in size. It may also be desirable for membranous or sheet structures, that, in porous form, do not possess sufficient tensile or burst strength, to undergo compression and fusion in select areas within the porous matrix for added mechanical strength. This compressed porous matrix material may be fabricated into many different devices for various applications in the body, which will be discussed later.

Any biocompatible polymeric material, which can to be fabricated into a porous matrix by those skilled in the art, is envisioned to be manufactured by the methods disclosed herein. Methods for creating a porous structure are well known to those skilled in the art (e.g., oil-water emulsions, lyophilization, precipitation, particulate leaching, critical gas blowing, gas forming polymerizations, etc.). As an example, one method involves dissolving a polymer in a solvent (e.g., acetone, chloroform, ethanol, dioxane, NMP, t-butanol, water, etc.) and filtering. The material is then treated to remove the residual solvent. Precipitating the polymer, evaporative distillation, lyophilizing the solution, or other methods may be used to remove the solvent, thus forming a porous polymeric material.

Another example involves dissolving a polymer in an organic solvent to prepare a polymer solution of high viscosity, or mixing a polymer solution in an organic solvent that does not dissolve the polymer to concentrate the solution as a gelatinous precipitate. A salt is homogeneously mixed with the polymer solution or gelatinous precipitate to give a polymer/salt/organic solvent mixed gel. The organic solvent is removed from the mixed gel through techniques known in the art (e.g., air dry, vacuum dry, sublimation, etc.) to produce an organic solvent-free polymer/salt composite. The composite is submerged in an aqueous solution or acidic solution to cause the salt to leach out to form a porous three-dimensional polymeric structure. The porous three-dimensional polymer structure useful for the present invention may contain open celled intercommunicating pores and/or closed celled non-communicating pores.

The resultant porous matrix material is compressed by force; preferably, at temperatures at or above the materials glass transition temperature, but below the melt temperature. Any method of compression known by those skilled in the art is conceivable for this invention, including, but not limited to, using hydraulically or pneumatically powered platens or pistons to compress the porous matrix material. Other methods include using a screw or an arbor press to compress the material. Compression is defined as a method for applying force to a porous matrix material in order to alter the size, shape, mechanical/material properties, and/or structure of the original material. The compression has many variables, including the amount of force/pressure used, the percent compression of the original height, the direction of compression, etc. The percent compression directly corresponds to the amount of porosity after compression. It should be noted that although compression reduces the overall porosity of the material, surface area of the pores is minimally affected. The compression temperature and hold time under pressure can also be varied to create the desired properties of the material. If desired, a focused combination of force, heat and time can be used to selectively fuse zones of a porous matrix. This is particularly useful when the starting porous structure is of such a low density or thickness and provides insufficient material or structure within the compressed zones as to provide the desired mechanical strength.

In another aspect of this invention, the starting porous matrix is granulated and in the form of porous particles or bodies. These porous particles are then compressed and sintered to create a final device composed of interpores and intrapores. Sintering is defined as a thermal treatment to promote spontaneous bonding and agglomeration reactions between particles. During this sintering step, porous particles bond together to create an open-celled porous matrix material. Sintering may be achieved through the thermal treatment alone, or more commonly, though not necessarily, sintering may be employed in combination with a compressive force. The preferable temperatures used in this sintering process are at or above the materials' glass transition temperature, but below the melt temperature. By starting with porous particles, more fabrication methods and material combinations are possible. In addition, not only can the polymer particles be porous, there may also be a mixture of porous and solid particles. Furthermore, dissimilar materials may be combined to create a sintered product; for example, ceramic particles may be mixed with the polymer-based particles to create a coherent sintered mass of ceramic and polymer. Porous particles can also be sintered and fused to larger solid or porous structures such as structures in the form of strips, block, rods and sheets.

Those skilled in the art will recognize that polymers without a glass transition temperature can still be utilized in creating the above-described invention by means of inducing pseudo-glass transitions. The simplest means of creating a pseudo glass transition is by incorporation of a plasticizer or plasticizing the polymer with small amounts of solvent. Other methods include, but are not limited to, quenching and cycling the temperature just above and below the melt point of the polymer. One skilled in the art will also recognize that these methods for creating pseudo-glass transition may also be effectively utilized for polymers having glass transition states. When creating a porous matrix by starting with multiple porous bodies such as two or more blocks, sheets, particles or combinations thereof the pseudo-glass transitions can also be achieved through the use of binders, solvents or plastisizers to bond the porous bodies together instead of sintering. For example, at ambient temperature, solvent vapors can be used to make the porous bodies tacky. Compression collapses the porous particulates wherein the newly contacting surfaces weld together. Vacuum can be use to speed removal of the solvent.

Another aspect of this invention relates to controlled stretching and molding of a porous matrix material. Heating to temperatures above the glass transition temperature allow the porous polymer to soften and contract. If contraction is prevented and a force in a new direction is applied, the malleable polymer can be stretched to the extent that the porosity can collapse and/or warp, allowing the porous matrix to be pressed into or over a mold. Cooling at this time will lock in the new shape. The area of polymer that has been shaped is different than the unaltered areas. This is due to the forced alignment of the polymer partitions. Molds may be tailored to impart anisotropic effects at discrete locations throughout the implant, by creating areas of higher flow (i.e., more stretching) as well as areas of very low flow. Therefore, properties may be tailored by location and degree. Unlike the compressing method described above, this method has the ability to increase the surface areas through pore elongation within the porous matrix as the porosity is reduced.

Use of glass transitional deformation can be used to mold specific attributes into a porous matrix material. This can be as simple as incorporating the impression of a company logo or as complicated as compressing the matrix material into a complicated mold giving it the appearance, for example, of a single bone in the hand or fingers. When using granulated porous particles as the starting material for this aspect of the invention, even more opportunities are apparent for molding or forming this material into a final porous matrix as well as creating variations within the implant by varying the amounts of granules in different parts of a mold. In addition, the mixture of various types of porous particles such as hydrophobic, hydrophilic, drug infused, and different polymers can create unlimited combinations of finished implants. This has the added advantage of creating variations in the type and location of degradation within the implant thereby providing for more controlled cell infusion, drug delivery, etc. Porous particles can also be fused to, or encased in a rolled or formed porous sheet thus ensuring that individual particles will not inadvertently slough off during handling.

Those skilled in the art will recognize from the previously explained summary of invention that this idea of compressing porous matrix materials can also be expanded to include using combinations of compressed porous matrices with compressed porous particles to create laminations of different porous materials.

Those skilled in the art will also recognize from the previously explained summary of invention that select areas of one or more porous bodies can be sheltered from compression, thus creating zones, islands or pockets of unaffected porous matrix surrounded by compressed areas of matrix Leaving zones of unaffected porous matrix surrounded by compressed areas of matrix produces a prosthesis, which, when implanted into a mammalian host, undergoes controlled biodegradation accompanied by adequate living cell replacement, such that the original implanted prosthesis is remodeled by the host's cells before it is degraded by the host's enzymes and/or by hydrolysis. The device of the subject invention is structurally stable, pliable, semi-permeable through the unaffected porous matrix, and suturable through the compressed areas of matrix.

Various embodiments of this invention can be utilized to repair, augment, or replace diseased or damaged organs, such as rotator cuff injuries, dura defects, abdominal wall defects, pericardium, hernias, and various other organs and structures including, but not limited to, bone, periosteum, perichondrium, intervertebral disc, meniscus, articular cartilage, dermis, epidermis, bowel, ligaments, tendon, vascular or intracardiac patch, or as a replacement heart valve.

The device if this invention could be used for sling procedures (e.g., surgical methods that place a sling to stabilize or support the bladder neck or urethra). Slings are typically used to treat incontinence. Additionally, in the form of a biphasic surgical mesh, the device can be used for such applications as hernia and dura repair.

In another embodiment, this invention provides a ligament or tendon repair or replacement prosthesis that is biocompatible, is able to withstand forces subjected to ligaments and tendons, and promotes healing of the injured tissues by acting as a scaffold for cellular infiltration while at the same time presenting compressed areas to provide mechanical strength. Another embodiment of this invention is to provide an improved disc replacement or prosthesis that is biocompatible, does not interfere with normal vertebral segment motion, is able to withstand normal spinal column forces, does not wear into the surrounding bone, provides low porosity zones for attachment to the surrounding vertebra using screws, stables, or other fasteners, promotes regrowth of intervertebral disc material, and high porosity zones that act as a scaffold for fibrocartilage infiltration.

The tissue repair implant of this invention, functioning as a substitute body part, may be flat, tubular, hollow or of complex geometry depending upon the intended use. Thus, when forming the structure of the prosthesis of this invention, a mold or plate can be fashioned to accommodate the desired shape.

Flat sheets may be used, for example, to support prolapsed or hypermobile organs by using the biphasic sheet as a sling for those organs or tissues (e.g., bladder or uterus). Tubular grafts may be used, for example, to support or reinforce tubular organs such as esophagus, trachea, intestine, and fallopian tubes.

The tissue repair implant of the present invention presents porous zones to permit the in-growth of host cells for remodeling or for deposition of the collagenous layer. The device can present "non-porous" zones to improve mechanical properties and prevent the passage of fluids if necessary or the porosity can be adjusted to create a membrane capable of selective permeability. The degree of porosity will affect mechanical properties of the implant, and these properties are also affected by processing.

The mechanical properties include mechanical integrity, such that the tissue repair implant resists creep for the necessary period of time, and additionally is pliable (e.g., has good handling properties) and suturable. The term "suturable" means that the mechanical properties of the layer include suture retention, which permits needles and suture materials to pass through the prosthesis material at the time of suturing of the prosthesis to sections of native tissue. During suturing, such prostheses must not tear as a result of the tensile forces applied to them by the suture, nor should they tear when the suture is knotted. Suturability of tissue repair implant, i.e., the ability of prostheses to resist tearing while being sutured, is related to the intrinsic mechanical strength of the prosthesis material, the thickness of the prosthesis, and the tension applied to the suture. The mechanical integrity of the prosthesis of this invention is also exhibited in its ability to be draped or folded, as well as the ability to be cut or trimmed or other shaping of the prosthesis.

In another embodiment of the invention, reinforcing elements (e.g., threads, fibers, whiskers, textiles, etc.) are incorporated into the tissue repair implant for reinforcement or for different rates of remodeling. Thus, the properties of the tissue repair device can be varied by the geometry of the thread used for the reinforcement. Additionally, thread constructs such as a felt, a flat knitted or woven fabric, or a three-dimensional knitted, woven or braided fabric may be incorporated between layers or on the surface of the construct.

An embodiment of the present invention may be made by the following steps: providing a plurality of polymer fibers and subjecting the fibers to at least one compressive force across isolated zones followed by application of heat. The compressive force causes compaction of the fibers and fuses them at temperatures below the melt point of the polymer. The plurality of fibers may include multiple polymers and may further comprise a mixture including biologically active agents, reinforcing agents or mixtures thereof. Additionally, lubricants and binders may be used to assist in fiber movement during compression and fusion.

The compressive force may be applied by a molding surface, thereby creating a shaped porous member in the mold. In one embodiment, the mold compresses or shapes only a portion of the porous member, thereby yielding a shaped porous member having both high and low porosity zones. In a another embodiment, the molding surfaces may be such as to provide one or more penetrating holes in the shaped member, specifically by pushing aside material such that the material becomes distorted circumferentially around each hole. These holes can exist within the low porosity zone, the high porosity zone or both zones. Additionally, or alternatively, the material may be machined, cut or punched thus allowing the fabrication of complicated shapes.

The strength of the biphasic device presenting low and high porosity zones may be tailored by a reinforcing element, such as particulates, threads, fibers, whiskers, textiles, rods, meshes, or combinations thereof. The function or properties of the implant may also be affected by additives, such as ceramics, polymers, cells, biologically active agents, liquids, surfactants, plasticizers, and combinations thereof.

Various medical uses of the above-described invention are described below. Other features or advantages of the present invention will be apparent from the following drawings and detailed description of the invention, as well as from the claims.

DESCRIPTION OF THE DRAWINGS

FIG. 6A is a perspective view of one embodiment of the implant.

FIG. 6B is a perspective view of one embodiment of the implant containing an osteogenic material.

FIG. 6C is a perspective view of the embodiment from FIG. 6A and one of the anatomical locations that is suitable for treatment by the implant.

DETAILED DESCRIPTION OF THE PREFERRED EMBODIMENTS

Figure 1A:
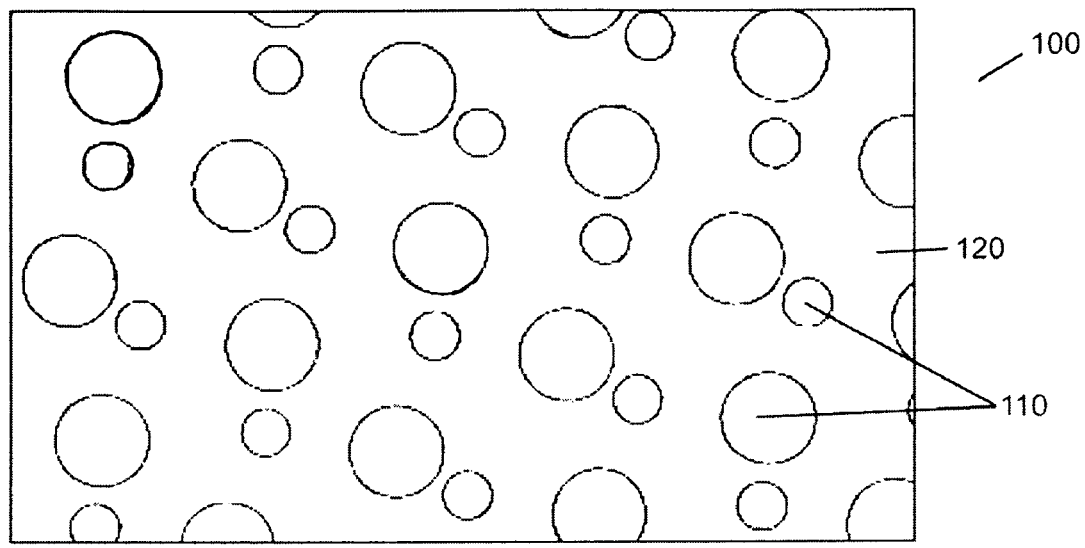
FIGS. 1A and B illustrate the porous matrix material, including its pore structure, before (1A) and after (1B) being compressed.

The object of the invention is an implantable prosthesis, constructed of a compressed porous polymeric material. The construction of the prosthesis is such that it is capable of absorbing energy and supporting large loads utilizing less mass of material than would be necessary in the formation of a solid polymer prosthesis. Additionally, the device has advantages over non-degradable solid implants, including the resorbable nature of the prosthesis, the ability to absorb biologically active materials, and the transient nature of its stress shielding.

While working to create a low porosity material, a new and unique method to control or alter the porosity within a porous material was discovered. In an embodiment, the method for preparing the high-density porous matrix involves:
 a) creating a high porosity polymeric matrix by methods known in the art;
 b) inducing glass-transition within said porous polymeric matrix;
 c) applying a compressive force within one or more dimensions to achieve a new size or shape; and
 d) cooling the porous polymer out of the glass-transition wherein the polymer matrix maintains the new size or shape.

Within this embodiment, steps b and c may be reversed such that the compressive force is applied and maintained then glass-transition temperatures are induced in said matrix.

A method of producing a high density porous matrix that may experience glass transition after being compressed to a new size or shape involves:
 a) creating a high porosity polymeric matrix by methods known in the art;
 b) inducing glass-transition within said porous polymeric matrix;
 c) applying a compressive force within one or more dimensions to achieve a new size or shape;
 d) holding the porous polymer matrix above glass transition at the new size and shape for a period of time allowing the molecular chains within the matrix to rotate or move to a lower energy state; and
 e) cooling the porous polymer out of the glass-transition wherein the polymer matrix maintains the new size or shape.

Within this method, it is also possible to reverse steps b and c such that a compressive force is applied below the glass transition temperature then heat is added to the material to take it above its glass transition temperature while it is held at a set dimension.

A method of producing a high density, high strength porous matrix sheet containing low-density zones involves:
 a) creating a high porosity polymeric matrix sheet by methods known in the art;
 b) inducing glass-transition within said porous polymeric matrix sheet;
 c) applying a compressive force over at least a portion of the polymer matrix sheet, within one or more dimensions, as may be accomplished using a plate containing shaped cavities, wherein the shaped cavities allow for less compression than the areas of the plate surrounding the cavities to achieve a new size or shape;
 d) holding the porous polymer matrix sheet above glass transition at the new size and shape for a period of time allowing the molecular chains within the matrix sheet that are under compression to rotate or move to a lower energy state; and
 e) cooling the porous polymer to below the glass-transition wherein the polymer matrix sheet maintains the new size or shape.

Within this method, it is also possible to reverse steps b and c such that a compressive force is applied below the glass transition temperature then heat is added to the material to take it above its glass transition temperature while it is held at a set dimension. Within this method it is also possible to apply enough force, temperature or time while above glass transition to allow the areas under compression to melt and flow creating high-density zones with little or no porosity. Within this method it is also possible to layer two or more sheets together wherein only the areas under compression fuse together, while the areas not subjected to compression within the shaped cavities do not fuse together. Within this method it is also possible to layer a particulate or fibrous material between the two layers wherein the particulate or fibrous material will be fused within the zones under compression while particulate or fibrous material protected by the cavities will be unbound within non-fused pockets created by the cavities.

As an additional embodiment of this invention, the starting porous matrix material may be provided as granular or particulate materials. The granular materials may be manufactured by various techniques known in the art, for example, a block of material may be processed through additional steps (e.g., mechanical shredding, granulation, etc.) to be transformed into particles. The particles provided may be porous, or non-porous, and preferably are resorbable. Alternatively, one skilled in the art would recognize other methods for creating porous particles suitable for use in this embodiment, such as a supercritical fluid technique, where the supercritical fluid process results in porous materials. These porous particles can then be compressed and sintered in a mold to make a finished medical implant.

Those skilled in the art will recognize porous materials that are characterized by being: not brittle and/or not susceptible to fracture (e.g. elastic polymers); or having partitions between individual pores that are thin enough so as to not need to be at glass transition prior to the application of a compressive step in order to avoid fracturing. It is recognized there may be a benefit to placing the materials in a state of glass transition while maintaining them in a compressive state in order to lock the material into the new conformation. Additionally, glass-transition may not be necessary for porous materials that do not naturally re-expand (e.g., porous metal) or that have been or will be contacted with a second substance that serves as a binder (e.g. bio-glue, adhesive, polymer solution) to lock the porous polymeric matrix in the compressed state. This binder can be an external coating or a substance that is flowed into the porosity and functions to hold the overlapping laminate walls together post compression. This binder may also be a temporary (e.g. biodegradable, dissolvable, heat sensitive) material that allows the compressed porous material to re-expand at a later time. This can be useful in filling voids that have small openings or for delivery of a compressed pellet through a cannula to a surgical site (e.g. spine, aneurism) where it is allowed to re-expand and provide support. It would be obvious to one skilled in the art that a binder would not be necessary for a re-expanding foam if the compressed foam only re-expanded when placed in contact with body fluids or at body temp.

When the porous matrix material is compressed, some or all of the pores may be sacrificed and collapse to form laminate walls. The pores are limited in the amount they may move within the material structure before they must absorb the compression and/or torque. Some pores are sacrificed, giving way to other pores, which may stay structurally intact giving the matrix material a unique toughness not seen in prior art materials. Depending on the method, direction, and amount of compression, the sacrificed pores could give way in different modes (e.g., collapsing, folding, slipping, reducing in overall size, narrowing, etc.). The movement of some pores within the material and the sacrificing of other pores may cause the material to compress, thus changing the material and mechanical properties of the porous matrix material. The collapsing of the pores will have a direct effect on the porosity of the porous matrix material. The porosity will decrease during compression as pores are sacrificed and relieve compressive stress. The term "sacrificed" is used to both describe the initial collapse of pores during manufacturing and any further changes to the pores in response to forces on the finished device. Toughness is partially imparted by the ability of a localized area within a device to independently accommodate stresses.

Compression can create a new structure within the porous matrix material. Certain compression methods may create collapsed pore walls that form thin, overlapping laminate walls. The laminate walls may be adjacent to each other, as in the case where compression has been applied to completely collapse the pores. Alternatively, the laminate walls may have some space or material between the walls, such that they are not in direct contact with each other (i.e., not adjacent). Because the laminate walls are formed from the collapsed pores, the layers are limited in the amount that they can slide, thus eliminating a delaminating or sliding mode of failure. Variations in the compression method and parameters can create collapsed pores that did not form thin laminate walls, but instead pores are condensed to a fraction of their original size. Because pores closest to the applied force typically collapse or give way first, the pores throughout the material may vary in size, creating an altered pore size distribution throughout the material. Given walls of equal thickness, larger pores are more likely to collapse than smaller pores. This can be used to reduce overall variation in pore size. Other methods for compression can produce tubular pores that are narrowed, lengthened, and/or collapsed. The tubular pores can span the length of the material or be interconnected. In all cases, compression parameters may be modified to produce material suitable for end use as a medical device.

The structure of the porous matrix material also depends on the amount of compressive force applied to the material. The amount of compression may change the porosity of the porous matrix material. The pore size distribution will also be affected by the amount of compression as the porous matrix material may be compressed so that only certain areas have collapsed pores, or so that all of the pores are sacrificed and collapse. The direction of compression in relationship to the original structure of the porous matrix material can also affect the structure of the compressed porous matrix material. For example, if the initial porous matrix material has long tubular columns, a force applied circumferentially to the material will collapse the diameter of the columns; whereas a force applied parallel to the axis of the columns will shorten the column length.

Compression of the porous matrix material can be controlled to create various structural patterns within the material; likewise, the mechanical properties of the material may be altered to meet specific requirements. The amount of compression is directly related to the maximum compressive load of the material. The more the material is compressed, the greater the maximum compressive load will be. If a medical device fabricated from the compressed material must withstand loading from more than one direction, the compressed material can be compressed three-dimensionally to increase the mechanical strength of the material in all directions. If the medical device is axially loaded, the compressed material may be compressed in one direction to optimize the mechanical properties of the material in that direction.

Generally, solid non-elastic, non-porous polymeric materials (i.e., polylactides, poly-dl-lactide, etc.) have good mechanical strength; however, they are brittle and will catastrophically fail under high compressive loads. Compressed porous material exhibits more ductility and toughness compared to the same non-porous polymeric material. The compressive porous material has the ability to absorb energy by sacrificing pores. As compression continues beyond the point when all the pores have collapsed, the material may expand slightly and microcracks will occur along its surface, thus avoiding catastrophic failure.

Elastic porous material may be used for soft tissue applications, and can be utilized to repair, augment, or replace diseased or damaged organs, such as rotator cuff injuries, dura defects, abdominal wall defects, pericardium, hernias, and various other organs and structures including, but not limited to, bone, periosteum, perichondrium, intervertebral disc, articular cartilage, dermis, epidermis, bowel, ligaments, tendon, vascular or intra-cardiac patch, or as a replacement heart valve.

The device of this invention could be used for sling procedures (e.g., surgical methods that place a sling to stabilize or support the bladder neck or urethra). Slings are typically used to treat incontinence. Additionally, in the form of a surgical mesh, the device can be used for such applications as hernia and dura repair.

Preferably, porous polymeric materials (fibrous and/or non-fibrous) are compressed for the present invention, although it is also envisioned that porous metallic materials (fibrous and/or non-fibrous) may also be compressed. It should be noted that many of the benefits imparted to polymeric materials, including ductility and toughness would also be imparted to compressed porous metallic materials. Thus it is another object of the invention to create improved, lightweight porous metallic implants useful in orthopedic surgery (e.g., artificial hip implants, bone plates, femoral nails, screws, etc.).

The temperature of the porous matrix material (e.g., glass transition temperature) during compression can greatly affect the behavior of the final material. More specifically, the relationship between the compression temperature and the material's glass transition temperature plays a vital role in the properties of the final material. Glass-transition is defined as the state during which the molecules making up the matrix are free to move and rotate in an effort to achieve a lower energy state. At temperatures narrowly above the glass transition temperature, and below the melting temperature, the molecule alignment will occur more slowly than would alignment at temperatures further above glass transition, but still below melting temperature. Those skilled in the art will recognize that polymers with an extremely high glass transition temperature, or even no glass transition, can still be utilized in creation of the present invention by means of inducing pseudo-glass transitions. The simplest means of creating a pseudo-glass transition is by the incorporation of a plasticizer or plasticizing the polymer with small amounts of solvent. This can be done by blending a plasticizer into the polymer or exposing the polymer to an atmosphere of molecules that would solvate the polymer at higher concentrations. Other methods include, but are not limited to, quenching and cycling the temperature just above and below the melt point of the polymer. Quenching allows crystalline polymers to become amorphous for a short period of time and may in turn create a pseudo-glass transition below the melt point of the polymer. Cyclic heating and cooling of a polymer just above and below its melt point can be used to simulate a glass transition by retarding collapse of the porous structure.

If the material is compressed below the glass transition temperature, stress can be locked into the material. If the material is then exposed to a temperature at or above the glass transition temperature, the stress will be relieved and the porous matrix material may expand and possibly return to its pre-compression dimensions. Yet, if the material is compressed at a temperature at or above the glass transition temperature or brought up to glass transition after compression while still being compressed, the polymer chains in the material are free to rotate and assume a lower energy state. This may eliminate the stress in the compressed material and the material will retain its dimensions even when exposed to temperature at or above the polymer's glass transition temperature for a period of time.

If not compressed initially into the final shape, after being compressed and removed from the compression device, the porous matrix material may be machined, punched or cut into a new shape or design with various features. Machining processes for polymeric materials are well known to those skilled in the art. (e.g., coring, milling, sawing, lathing, etc.) As an example, a tubular device could be machined by coring out the inner diameter and then using a lathe to create the proper outer diameter. Punching or cutting of sheet materials is also well know to those skilled in the art and can include press punching with metallic cutting dies, laser cutting and water jet cutting.

The porous matrix material may be compression molded into an initial or final design of a medical device. If the device has complicated geometry, various features may be machined after compression molding, creating a refined shape for the device. As discussed above, the material and mechanical properties of the final device can be altered by the compression or mold temperature, the amount of overall compression, the design of the mold, etc. The porous matrix material may be compressed before molding or all the compression may occur during the molding process. The direction of compression before or during compression molding may also affect the mechanical properties of the device. For example, a cylinder of porous material may be three-dimensionally compressed and then compression molded into a threaded bone screw. Additionally, if the mold is heated and compression is performed rapidly, only those areas in direct contact with the mold will achieve glass transition, and collapse in response to compression. In this manner, a device having bi-modal pore structure can be created, as the pores in the center remain unaltered by compression.

The prosthesis may be sterilized by any method known in the art (e.g. exposure to ethylene oxide, hydrogen peroxide gas plasma, e-beam irradiation or gamma irradiation, etc.). The sterilization process minimizes the opportunity of infection to occur as a result of the implant.

In an embodiment of the invention, a porous medical device is manufactured from a resorbable material, although this is not meant to exclude the use of non-resorbable polymers and metals. Different polymers, molecular weights, additives, processing methods, and sterilization methods can be used to control the resorption rates of resorbable polymers. Resorption rates can be adjusted to be shorter for applications that require mechanical strength for only a short period of time or longer for applications that require mechanical strength to be present for a longer duration. The materials of the construct may be fibrous or non-fibrous. Examples of resorbable polymers that can be used to form medical devices are shown in Table 1. These materials are only representative of the materials and combinations of materials, which can be used as implant materials.

TABLE 1

Examples of Bioresorbable Polymers for Construction of the Material of the Current Invention.

Alginate
Aliphatic polyesters
Cellulose
Chitin
Chitosan
Copolymers of glycolide
Copolymers of lactide
Elastin
Fibrin
Glycolide/l-lactide copolymers (PGA/PLLA)
Glycolide/trimethylene carbonate copolymers (PGA/TMC)
Glycosaminoglycans
Lactide/tetramethylglycolide copolymers
Lactide/trimethylene carbonate copolymers
Lactide/e-caprolactone copolymers
Lactide/s-valerolactone copolymers
L-lactide/dl-lactide copolymers
Methyl methacrylate-N-vinyl pyrrolidone copolymers
Modified proteins
Nylon-2
PHBA/g-hydroxyvalerate copolymers (PHBA/HVA)
PLA/polyethylene oxide copolymers
PLA-polyethylene oxide (PELA)
Poly (amino acids)
Poly (trimethylene carbonates)
Poly hydroxyalkanoate polymers (PHA)
Poly(alklyene oxalates)
Poly(butylene diglycolate)
Poly(hydroxy butyrate) (PHB)
Poly(n-vinyl pyrrolidone)
Poly(ortho esters)
Polyalkyl-2-cyanoacrylates
Polyanhydrides
Polycyanoacrylates
Polydepsipeptides
Collagen
   Types 1 to 20
      Native fibrous
      Soluble
      Reconstituted fibrous
      Recombinant derived
Polydihydropyrans
Poly-dl-lactide (PDLLA)
Polyesteramides
Polyesters of oxalic acid
Polyglycolide (PGA)
Polyiminocarbonates
Polylactides (PLA)
Poly-lactide/Poly-caprolactone copolymers (PLA/PCL)
Poly-l-lactide (PLLA)
Polyorthoesters
Poly-p-dioxanone (PDO)
Polypeptides
Polyphosphazenes
Polysaccharides
Polyurethanes (PU)
Polyvinyl alcohol (PVA)
Poly-b-hydroxypropionate (PHPA)
Poly-b-hydroxybutyrate (PBA)
Poly-s-valerolactone
Poly-b-alkanoic acids
Poly-b-malic acid (PMLA)
Poly-e-caprolactone (PCL)
Pseudo-Poly(Amino Acids)
Starch
Trimethylene carbonate (TMC)
Tyrosine based polymers For the purposes of promoting an understanding of the principles of this invention, reference will now be made to the embodiments illustrated in the drawings, where like numbers refer to like components, and specific language will be used to describe the embodiments and elements of the embodiments. It must be understood that no limitation of the scope or applications of the invention is thereby intended. For ease of understanding, pores are represented in the drawings by closed circles, it is recognized the pores may in fact be formed in various shapes, textures and interconnectivity (e.g., they may be interconnected or separate, open cell or closed cell, organized or random, and/or reticulated structures).

Figure 1B:
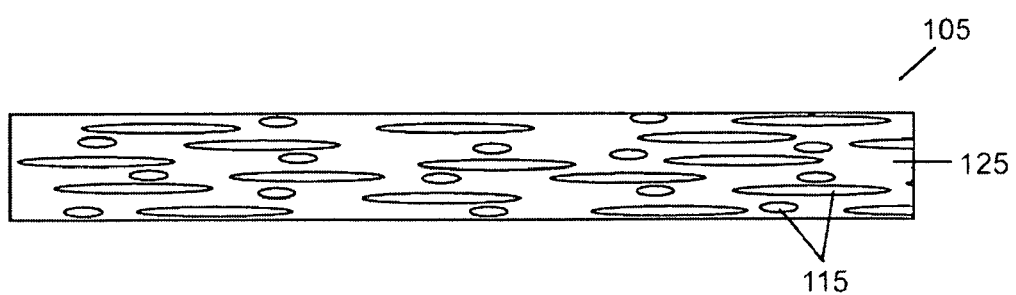

Referring now to the drawings, FIG. 1A depicts the porous matrix material 100 before any compressive force has been applied. The porous matrix material 100 includes a large percentage of void space, which is occupied by pores 110. The pores 110 form the structure within the polymeric material 120. After being compressed, as depicted in FIG. 1B, the compressed porous matrix material 105 contains the same amount of polymeric material 125; however, the sacrificed, collapsed pores 115 have reduced the porosity of the material.

Figure 2A:
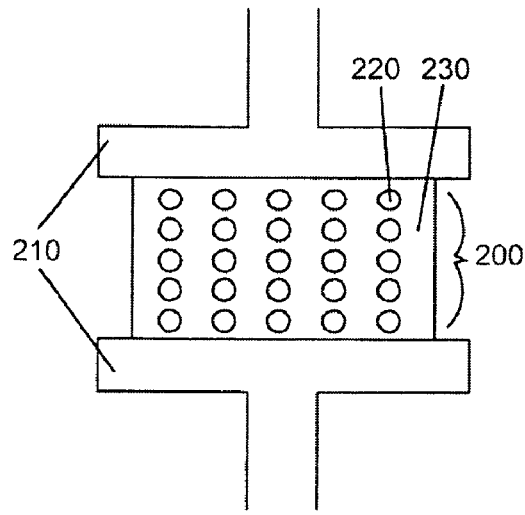
FIG. 2A illustrates the porous matrix material between two compressive devices.

In another embodiment, as depicted in FIG. 2A, uncompressed porous matrix material 200 is placed between two devices capable of applying compressive force 210 (e.g., platens, pistons, etc.), which may or may not be heated. The pores 220 and polymer material 230 define the structure of the uncompressed porous matrix material.

Figure 2B:
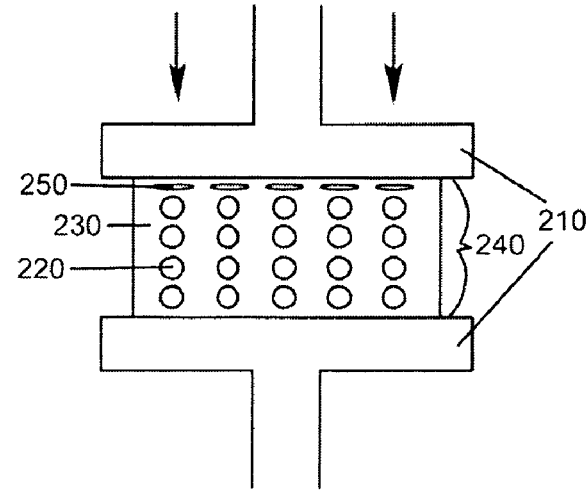
FIG. 2B shows the porous matrix material being compressed by the top compressive device.

As depicted in FIG. 2B, the compressive device 210 is actuated to create partially compressed porous matrix material 240. Upon compression of the material 240, a gradient is formed, wherein the compressed pores 250 first begin to collapse, while the pores 220 (depicted here in FIG. 2B as the lower part of the material) furthest removed from the actuated compressive device 210 retain their original structure. This can be employed to create an implant for biphasic tissues such as bone. The portion containing the collapsed pores 250 resembling cortical bone and the remaining portion remaining uncompressed 220 resembling cancellous bone.

Figure 2C:
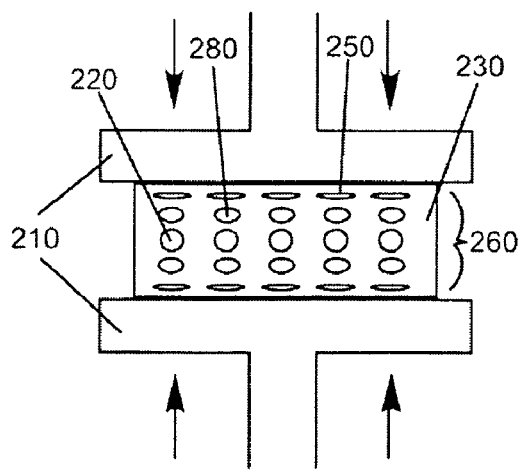
FIG. 2C shows the porous matrix material being compressed by both compressive devices.

As shown in FIG. 2C, dual gradient porous matrix materials 260 can be formed by compressing the porous matrix material with a plurality of actuated compressive devices 210, actuated either in succession or simultaneously. The compressed surfaces, containing the pores closest to the actuated compressive devices 210, will contain the highest proportion of sacrificed or compressed pores 250. The next layer contains the partially compressed pores 280 which have started to collapse, but initially will decrease in size before completely collapsing or being sacrificed. The porous matrix material furthest removed from the actuated compressive devices 210, in the middle of the dual gradient material 260, will have pores 220 that most closely maintain their original structure and size. This multiple compression technique depicted in FIG. 2C may be employed to create an implant for a triphasic tissue such as the skull, requiring an implant that mimics the transitions from cortical bone (more solid) to cancellous bone (porous) and back to cortical bone.

Figure 2D:
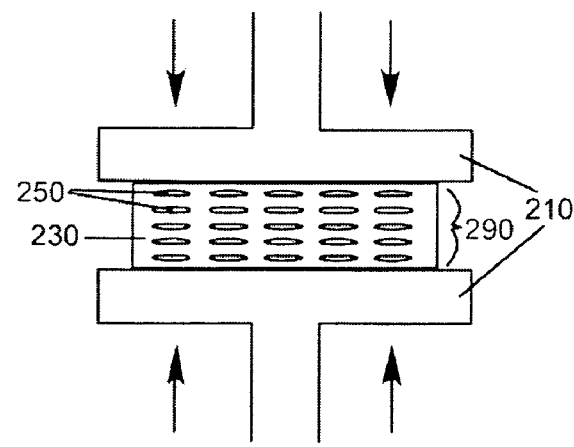
FIG. 2D shows the porous matrix material being compressed by both compressive devices in a heated atmosphere.

As shown in FIG. 2D, an evenly and significantly compressed porous matrix material may be created, such as by actuating the compressive devices 210 acting upon porous matrix material, by completely collapsing and sacrificing every pore. As a result, the evenly and significantly compressed material could be formed without any of the gradients created in devices of FIGS. 2B and 2C. As seen in FIG. 2D, the sacrificed or collapsed pores 250 can be distributed throughout the material 290. This is useful in the creation of a superior implant to replace those currently manufactured from cortical bone, metal, or solid polymers.

An evenly compressed porous matrix material 290 may also be created by actuating the compressive devices 210 upon the material, while it is exposed to a heated atmosphere (e.g., convection oven, environmental control chamber, etc.). The heated environment may be above the glass transition temperature of the polymeric material. As a result, an evenly compressed material 290 could be formed without being significantly compressed and without any of the gradients created in the devices of FIGS. 2B and 2C. As seen in FIG. 2D, the sacrificed or collapsed pores 250 will be evenly distributed throughout the material 290.

It is envisioned that desired percentages of porosity or desired pore shapes and sizes can be created based on the amount and method of compression. Specific pore shapes (e.g., spherical, thin flat sheet, tubular, etc.) or sizes may promote different types of tissue ingrowth (e.g. bone or vascular tissue ingrowth). Based on desired porosity or pore structure, the porous matrix material may act as a cellular scaffold for various uses in tissue engineering.

If desired, compressive devices 210 can contain cavities (not shown) or be shaped to reduce or eliminate the compressive force in select or isolated areas. This lack of compressive force creates a multi-phasic material having island or zones of increased porosity. In this document, multi-phasic refers to a device having at least two different regions or zones of compression. For example, a first phase of highly compressed material fused to a second phase of less compressed material.

In another embodiment, surfaces of the porous matrix material (whether partially compressed 240 depicted in FIG. 2B, a dual gradient material 260 in FIG. 2C, or evenly compressed 290 as shown in FIG. 2D) while in contact with actuated compressive devices 210, which may or may not be heated, could have compressed pores 250 forming extremely thin sheets. The extremely thin compressed pores 250 may form laminate walls, thus providing a confining matrix for confining new tissue growth within the device. This can be important for applications involving areas such as the spine where vital neural and vascular tissues are exposed and vulnerable.

Figure 3A:
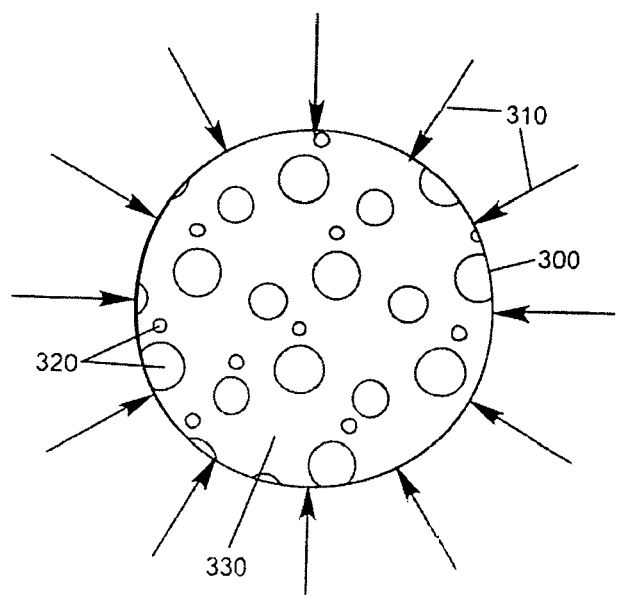
FIGS. 3A and B illustrate the three-dimensional compression of a porous matrix sphere, including its pore structure before (3A) and after (3B) being compressed.
Figure 3B:
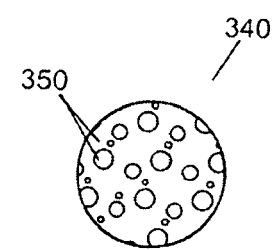

In another embodiment, as illustrated in FIG. 3A, an uncompressed shape, (e.g., a sphere) 300 of porous matrix material is to be subjected to compressive forces in three dimensions, with the compressive forces to be applied depicted by arrows 310. This three-dimensional compression may be applied in a variety of forms, for example mechanical means of compression, or alternatively by exposing the sphere 300 to a high pressure environment (e.g., increased atmospheric or hydrodynamic pressure). Pores 320 within a polymeric material 330 create the uncompressed sphere's 300 structure. As depicted in FIG. 3B, after application of compressive forces, the porosity and size of the compressed sphere 340 have been decreased. Unlike two-dimensional compression, the pores 350 have not collapsed into thin, laminate walls. The three-dimensional compression resulted in compressed pores 350, by reducing the pores in size, rather than inducing collapse. Alternately the decrease in the size of the sphere may be caused by folding of the pores resulting in a decrease in the constrained area within each pore, or an increase in wall thickness between the pores of the polymeric material (not shown). This embodiment may be implanted within the body for various purposes, for example as a device to promote staged delivery of biologically active agents or alternatively, the device or a section of the device may be used to create an implant in order to repair, replace or supplement a body part (e.g., a chin or a cheek). The embodiment of a three-dimensionally compressed shape may also be used to create a cell based implant wherein the cells supported in the non-compressed center of the device are protected from the body's immune system by the collapsed porous exterior. This would be particularly useful in supporting and protecting transplanted tissue (autograft or xenograft) such as islate cells capable of producing insulin. While immune cells would be prevented from entering the sphere 340 and destroying the islate cells, oxygen and nutrients would readily pass through the collapsed pores 350. In turn, waste product and insulin would pass out of the sphere.

Figure 4A:
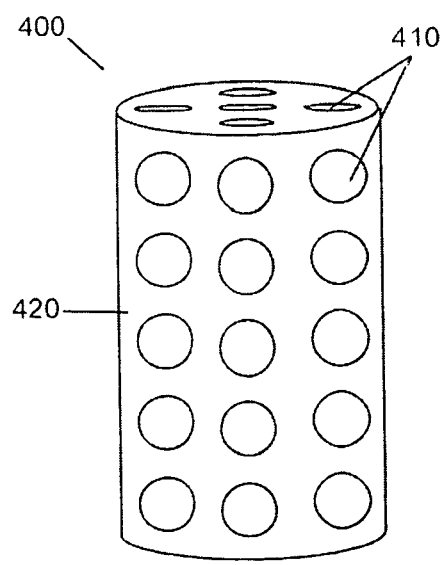
FIGS. 4A and B illustrates the three-dimensional compression of a porous matrix cylinder, including its pore structure before (4A) and after (4B) being compressed.
Figure 4B:
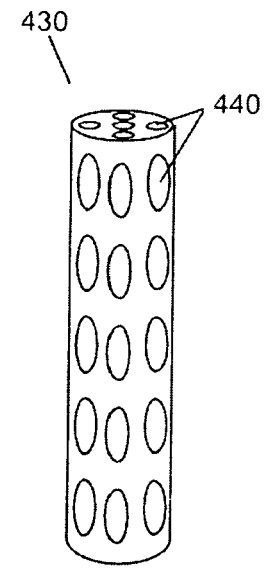

Two-dimensional compression may also be applied upon a shape (e.g., a cylinder) as illustrated in FIGS. 4A and 4B. Like the sphere 300 of FIG. 3A, the uncompressed cylinder 400 of FIG. 4A is composed of pores 410 within a polymeric material 420. Two-dimensional compression may be applied to the cylinder 400 by applying force around the circumference of the cylinder 400 while restricting elongation of its height. This type of two-dimensional compression may result in the smaller diameter compressed cylinder 430 of FIG. 4B. The compressed cylinder 430 may feature pores 440 that have been forced to narrow under two-dimensional compression yet maintain their relative height. If the elongation of the compressed cylinder 430 is encouraged (e.g., by tension applied at one or both ends of the cylinder), the pores within may narrow and lengthen (not shown). Depending on the amount of compression applied, the pores 440 could form thin tubes running parallel to each other throughout the height of the cylinder 430. Devices like this would be useful in various medical applications (e.g., as orthopedic rods, nerve guides, etc.).

It is recognized that the pores 440 can be compressed by a drawing or lengthening action of the cylinder 400. As porous materials are brought above glass transition, they soften and contract. If contraction is prevented and a force in a new direction is applied, the now malleable material may stretch to the extent that the porosity can collapse and the void volume is lost. This will allow the porous material to be shaped by being compressed into, stretched into, or drawn over a mold. In this way, porous sheet material (not pictured) can be stretched into concave molds or over convex molds allowing the formation of unique cup or cavity shaped sheets. In essence, the porous sheet material at or above glass transition can be thermoformed by any method known to those skilled in the art, including, for example, male/female molding and vacuum drawing. The area of the porous polymer that has been shaped is stiffer than the unaltered areas of the sheet. This is believed to be due to the forced alignment of the polymer partitions defining the pores.

The forced alignment of the pores can also be used to create a pseudo-elastic memory in non-elastic polymers. If a porous sheet is brought above glass transition and drawn in a single direction, the pores can collapse in the transverse direction while elongating in the longitudinal direction. After cooling below glass transition temperature, the sheet resists forces applied in the longitudinal direction, but will easily expand in the transverse direction by allowing the elongated collapsed pores to open up as the entire sheet shortens in the longitudinal direction. If the force in the transverse direction is released, the sheet springs back to its elongated form.

This process can also be applied to the compressed cylinder 430 in FIG. 4B. If the cylinder is compressed around its circumference with tension applied to both ends while being heated, the pores will be forced into alignment while being narrowed and lengthened. After cooling down, tension could be applied at various locations around the center of the cylinder. As the cylinder expands and bows in the middle, the central pores are widened, yet the top and bottom pores move closer to each other. When the tension is released, the cylinder and pores return to their normal compressed shape and size.

A device having elongated pores capable of widening movement in the transverse direction could be used as a ligament or tendon. In a tubular form, it could be useful as a vessel, nerve guide, esophagus or other tubular organs. Additionally, it could be used as a sleeve, sack, or bag stretched over or around implants (e.g., rods, nails, etc.) or used to hold materials, for example granular materials such as ceramics (e.g., hydroxyapatite, tricalcium phosphate, etc.), or other materials such as tissues (e.g., cells, bone chips, demineralized bone, bone marrow aspirate, etc.).

In another embodiment as illustrated in FIGS. 5A to 5D, a compressed polymer matrix material 500 may be created in a common shape (e.g., a block, a sheet, a sphere, etc.) and/or shaped, machined, or molded to fit a particular application, with the material further containing or coated with at least one additive component 530. These additives may be associated with only the surface 510 of the polymer matrix material, rather than extending into the interior of the shaped material (e.g., serving as a coating or shell). Alternatively, the additives 530 may be distributed throughout and incorporated into the material 500 and/or the pores 520, either in a random or non-random dispersion. In an embodiment of the device having a random dispersion of the additives 530, the additives may be uniformly distributed throughout the volume of the polymer matrix material 500. In another embodiment, the additive 530 may be distributed non-randomly, i.e., having a non-uniform distribution of additive 530 within the polymer material 500, or within, or forming, a depot within the material 500. The non-uniform distribution may impart a desired quality to the material (e.g., by selectively affecting a portion of the material 500, by providing the ability to deliver a drug or multiple biologically active agents as a burst and/or over an extended period of time, etc.). In another embodiment, the additives 530 may be associated with only the pores 520 within the polymer matrix material 500. In any of the embodiments containing additives, the pores may be open or closed cell, random or interconnected.

Figure 5A:
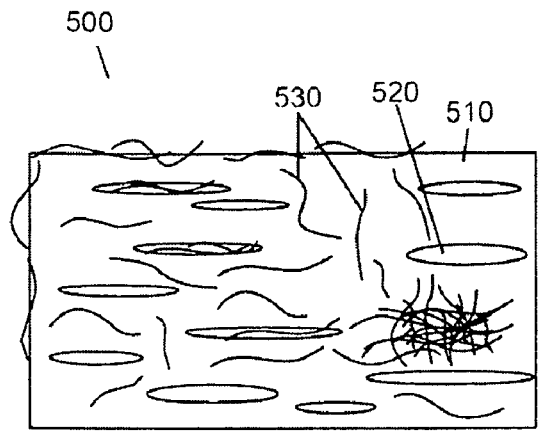
FIGS. 5A to 5D show the pore structure of compressed porous matrix material that contains various additive materials.

In one embodiment, at least one of the additives 530 of FIG. 5A may serve to reinforce the polymer matrix material 500. The reinforcing additives 530 serve to enhance the characteristics of the device, such as mechanical strength (e.g., modulus of elasticity, compressive strength, tensile strength, etc.) and biodurability (e.g., hydrolytic degradation, strength retention, etc.). This may be accomplished by incorporating reinforcing elements (e.g., mesh, fibers, threads, screen, etc.) onto the surface, or incorporated into the material 500 (e.g., uniformly dispersed or individual layers) and/or the pores 520 of the polymer material. To further improve the mechanical properties of the material, the reinforcing elements may be interwoven, layered, or compacted together during the manufacture of the uncompressed polymeric material, or as a result of compression in making the compressed polymeric material 500.

Figure 5B:
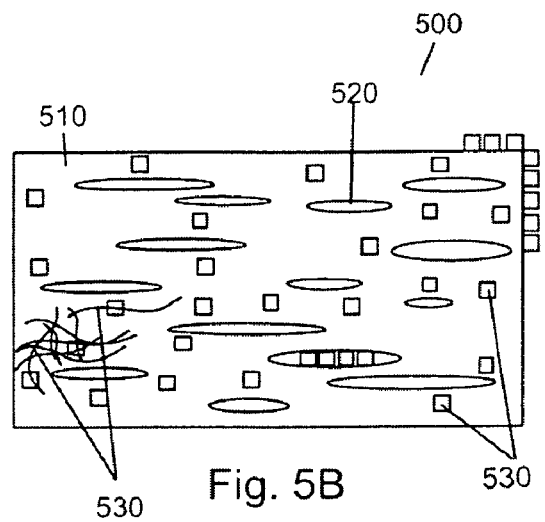
Figure 5C:
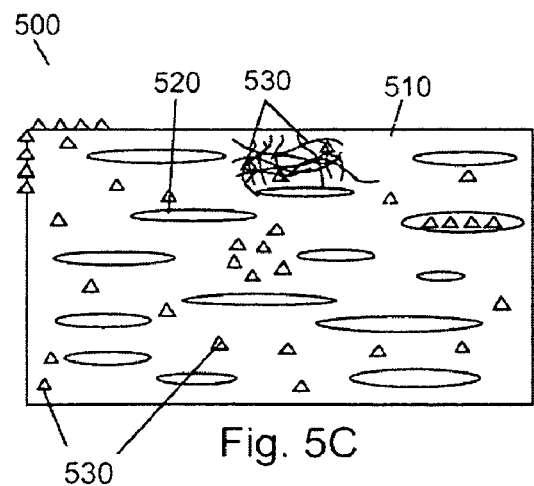
Figure 5D:
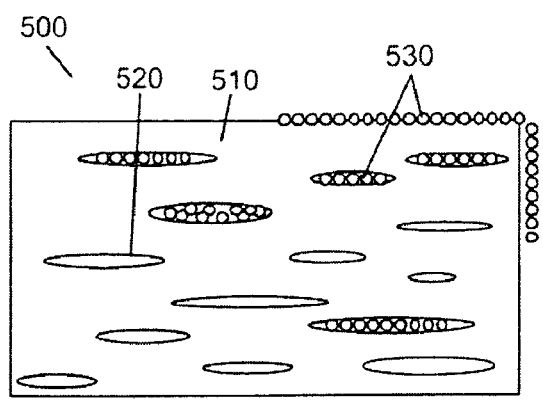

In another embodiment, at least one of the additives 530 of FIG. 5B may include or be a biologically active agent (e.g., growth factors, antibiotics, demineralized bone material, cells, drugs, viruses, blood, bone marrow aspirate, lipids, etc.). The unique porous structure of the compressed material 500 can be used to control the location and delivery of the biologically active agents. The formation of the construct controls the flow of fluid (e.g., blood, interstitial, etc.) within the device allowing for tailored release properties. The biologically active agents may be incorporated into the device along with reinforcing agents, in which case, it is recognized the biologically active agents may be mechanically or chemically attached or bonded to the reinforcing materials. Alternatively, it is also recognized that any of the additives 530 (e.g., reinforcing or biologically active agents) may be delivered together in the material 500 of the device without being mechanically or biologically bonded. Examples of biologically active agents that may be delivered in the device are shown in Table 2.

TABLE 2

Examples of Biological Active Ingredients

Adenovirus with or without genetic material
Alcohol
Amino Acids
    L-Arginine
Angiogenic agents
Angiotensin Converting Enzyme Inhibitors (ACE inhibitors)
Angiotensin II antagonists
Anti-angiogenic agents
Antiarrhythmics
Anti-bacterial agents
Antibiotics
    Erythromycin
    Penicillin
Anti-coagulants
    Heparin
Anti-growth factors
Anti-inflammatory agents
    Dexamethasone
    Aspirin
    Hydrocortisone
Antioxidants
Anti-platelet agents
    Forskolin
    GP IIb-IIIa inhibitors
        eptifibatide
Anti-proliferation agents
    Rho Kinase Inhibitors
    (+)-trans-4-(1-aminoethyl)-1-(4-pyridylcarbamoyl)
    cyclohexane
Anti-rejection agents
    Rapamycin
Anti-restenosis agents
    Adenosine $A_{2A}$ receptor agonists
Antisense
Antispasm agents
    Lidocaine
    Nitroglycerin
    Nicarpidine
Anti-thrombogenic agents
    Argatroban
    Fondaparinux
    Hirudin
    GP IIb/IIIa inhibitors
Anti-viral drugs
Arteriogenesis agents
    acidic fibroblast growth factor (aFGF)
    angiogenin
    angiotropin
    basic fibroblast growth factor (bFGF)
    Bone morphogenic proteins (BMP)
    epidermal growth factor (EGF)
    fibrin
    granulocyte-macrophage colony stimulating factor (GM-CSF)
    hepatocyte growth factor (HGF)
    HIF-1
    insulin growth factor-1 (IGF-1)
    interleukin-8 (IL-8)
    MAC-1
    nicotinamide
    platelet-derived endothelial cell growth factor (PD-ECGF)
    platelet-derived growth factor (PDGF)
    transforming growth factors alpha & beta (TGF-.alpha., TGF-beta.)
    tumor necrosis factor alpha (TNF-.alpha.)
    vascular endothelial growth factor (VEGF)
    vascular permeability factor (VPF)
Bacteria
Beta blocker
Blood clotting factor
Bone morphogenic proteins (BMP)
Calcium channel blockers
Carcinogens TABLE 2-continued Examples of Biological Active Ingredients Cells
Cellular materials
    Adipose cells
    Blood cells
    Bone marrow
    Cells with altered receptors or binding sites
    Endothelial Cells
    Epithelial cells
    Fibroblasts
    Genetically altered cells
    Glycoproteins
    Growth factors
    Lipids
    Liposomes
    Macrophages
    Mesenchymal stem cells
    Progenitor cells
    Reticulocytes
    Skeletal muscle cells
    Smooth muscle cells
    Stem cells
    Vesicles
Chemotherapeutic agents
    Ceramide
    Taxol
    Cisplatin
Cholesterol reducers
Chondroitin
Collagen Inhibitors
Colony stimulating factors
Coumadin
Cytokines prostaglandins
Dentin
Drugs
Etretinate
Genetic material
Glucosamine
Glycosaminoglycans
GP IIb/IIIa inhibitors
    L-703,081
Granulocyte-macrophage colony stimulating factor (GM-CSF)
Growth factor antagonists or inhibitors
Growth factors
    Bone morphogenic proteins (BMPs)
    Core binding factor A
    Endothelial Cell Growth Factor (ECGF)
    Epidermal growth factor (EGF)
    Fibroblast Growth Factors (FGF)
    Hepatocyte growth factor (HGF)
    Insulin-like Growth Factors (e.g. IGF-I)
    Nerve growth factor (NGF)
    Platelet Derived Growth Factor (PDGF)
    Recombinant NGF (rhNGF)
    Tissue necrosis factor (TNF)
    Transforming growth factors alpha (TGF-alpha)
    Transforming growth factors beta (TGF-beta)
    Vascular Endothelial Growth Factor (VEGF)
    Vascular permeability factor (UPF)
    Acidic fibroblast growth factor (aFGF)
    Basic fibroblast growth factor (bFGF)
    Epidermal growth factor (EGF)
    Hepatocyte growth factor (HGF)
    Insulin growth factor-1 (IGF-1)
    Platelet-derived endothelial cell growth factor (PD-ECGF)
    Tumor necrosis factor alpha (TNF-.alpha.)
Growth hormones
Heparin sulfate proteoglycan
HMC-CoA reductase inhibitors (statins)
Hormones
    Erythropoietin
Immoxidal
Immunosuppressant agents
inflammatory mediator
Insulin
Interleukins
Interlukin-8 (IL-8)
Interleukins
Lipid lowering agents TABLE 2-continued Examples of Biological Active Ingredients Lipo-proteins
Low-molecular weight heparin
Lymphocites
Lysine
MAC-1
Methylation inhibitors
Morphogens
Nitric oxide (NO)
Nucleotides
Peptides
Polyphenol
PR39
Proteins
Prostaglandins
Proteoglycans
    Perlecan
Radioactive materials
    Iodine - 125
    Iodine - 131
    Iridium - 192
    Palladium 103
Radio-pharmaceuticals
Secondary Messengers
    Ceramide
Somatomedins
Statins
Stem Cells
Steroids
Thrombin
Thrombin inhibitor
Thrombolytics
Ticlid
Tyrosine kinase Inhibitors
    ST638
    AG-17
Vasodilators
    Histamine
    Forskolin
    Nitroglycerin
Vitamins
    E
    C
Yeast
Ziyphi fructus The inclusion of groups and subgroups in the tables is exemplary and for convenience only. The grouping does not indicate a preferred use or limitation on use of any material therein. For example, in Table 2, the groupings are for reference only and not meant to be limiting in any way (e.g., it is recognized that the Taxol formulations are used for chemotherapeutic applications as well as for anti-restenotic coatings). Additionally, this table is not exhaustive, as many other drugs and drug groups are contemplated for use in the current embodiments. There are naturally occurring and synthesized forms of many therapies, both existing and under development, and the table is meant to include both forms.

In another embodiment, at least one of the additives 530 of FIG. 5A to 5D may be in the form of particulate components or filler materials (e.g., tricalcium phosphate, biphasic calcium phosphate, hydroxylapatite, calcium sulfate, tetracalcium phosphate, autologous bone graft, allograft bone matrix, polymers, microspheres, collagen, extracellular matrix, etc.), which enhance the functionality of the device. The particulate components may be delivered within the polymeric material 500 in various forms (e.g., granules, chips, powders, gels, etc.). The incorporation of particulate components into the polymeric material 500 may enhance the ability of the device to exhibit desirable biological qualities (e.g., cellular growth promotion, bioactive osteoconductivity, tissue ingrowth promotion, etc.). Furthermore, the particulate components may also serve to enhance the mechanical strength of the material. A non-exhaustive list of additive materials 530 that may be incorporated in the present invention in the form of particulate or filler materials is provided in Table 3.

TABLE 3

Examples of Particulate or Filler Materials Suitable for Use in the Invention

Alginate
Bioglass
Calcium
Calcium Phosphate
    Monobasic
    Dibasic
    Tribasic
Ceramics
Chitosan
Cyanoacrylate
Collagen
Dacron
Demineralized bone
Elastin
Extra Cellular Matrix
Fibrin
Gelatin
Glass
Gold
Hyaluronic acid
Hydrogels
Hydroxy apatite
Hydroxyethyl methacrylate
Nitinol
Oxidized regenerated cellulose
Phosphate glasses
Polyethylene glycol
Polyester
Polysaccharides
Polyvinyl alcohol
Radiopacifiers
Salts
Silicone
Silk
Steel (e.g. Stainless Steel)
Synthetic polymers
Thrombin
Titanium In another embodiment, at least one of the additives 530 of FIG. 5A to 5D may serve to impart or create a microstructure within the macrostructure of the polymeric material 500. Preferably, the macrostructure may serve to maintain the mechanical, architectural, and structural stability of the device and provide a biologically inert surface for tissue ingrowth. The microstructure additive may, in an embodiment, serve to attract and nourish inbound cellular growth. The additive material 530 suitable for creating a microstructure can be selectively varied within certain regions of the macrostructure to promote or deter different biologic characteristics critical to different tissue requirements. The microstructure creating additive 530 could be contained by or concentrated within the compressed pores 520. The microstructure can be strategically located within one or more compressed pores 520. The microstructure creating additive 530 may also be on the surface 510 of the macrostructure. When located within collapsed intercommunicating pores, the microstructure may prevent complete collapse of the pore. The volume of microstructure can be used to control the percentage collapse of each pore. The space created by the microstructure, as well as the hydrophilic/hydrophobic properties of the microstructure, influence the rate at which fluids and/or cells flow into and out of the collapsed pores. In this way, microstructure could be used to control the release kinetics of other additive materials, such as biologically active agents, supported within the polymer or within the microstructure itself, from the device.

Additionally, a microstructure of the device may be hydrated, such that the fully hydrated microstructure helps to maintain fluid within the pores of the device. In this way the device is able to withstand greater compressive forces due to the non-compressibility of fluids, thereby acting as a hydraulic damper. For example, with a hydrophillic microstructure, the hydrophilicity of the microstructure tends to prevent the release of fluids as compression is applied, and only upon achieving a compression substantial enough to overcome the hydrophilic nature is the fluid released, thereby allowing the material to withstand greater compressive forces. Additionally, as the hydrophilic microstructure would have a tendency to take back in the released fluid as compression is released, there is a tendency to preserve the original volume, and shape of the device, enhancing the ability of the device to serve as a hydraulic damper.

It is recognized that any of the above-described additive agents 530 may be used alone or in combination with other additive materials. It is also recognized that individual components making up the additive materials may serve a dual purpose as an additive (e.g., acting as a biologically active agent and a reinforcing agent concurrently). When more than one additive 530 is used within the polymer material 500, the additives may function separately, or have a synergistic effect, wherein the activity of one class of additive 530 helps the activity of the other class of additive component 530. The additives may physically be bonded together, or merely be placed in proximity with each other, or even distributed randomly or non-randomly without any interrelationship. It is also recognized that based on the physical characteristics of the additive components, some of the components may not resorb or may resorb into the body at a different rate from other components, or have similar or different temporal qualities, such that the effects of the different additives may persist for various durations.

In another embodiment, shown in FIG. 6A, a resorbable spinal implant in the form of an interbody fusion device (e.g., spinal cage, spacer, wedge, etc.) 610 may be created from the compressed porous matrix material 600. An interbody fusion device 610, once implanted using techniques known in the art, may serve to restore the disc space in a spinal column. An interbody fusion device created utilizing the material 600 of the present invention may be used to provide a large surface area to provide for adequate bone ingrowth, thereby eliminating the need for the prior art technique of bone harvesting for autografts to be used in creating a spinal implant.

The device of the present invention may also be constructed as a spinal implant for posterolateral fusion (not shown). A posterolateral spinal implant spans and contacts the transverse processes of adjacent vertebrae. The posterolateral implant made in accordance with the present invention will maintain a space above and across the transverse processes and facilitate new bone formation.

In an embodiment, the device may be constructed as an anterior fusion spinal implant (not shown). An anterior spinal implant would fasten to two vertebrae and span the operative disc space, thereby serving to restrict motion and promote fusion through bone growth.

In an embodiment of the present invention, the compressed pores 620 within spinal implant device 610 may be of any size or shape and arranged in any orientation suitable for use as a spinal implant. Preferably, the compressed pores 620 would be formed as thin, laminate sheets, which enable the device 610 to withstand both large compressive loads and cyclic loading. In some embodiments, the structure and design of the device 610 will give it desirable mechanical properties (e.g., compressive strength, modulus of elasticity, tensile strength, etc.) similar to cortical and/or cancellous bone.

In another embodiment, one or more channels 630 (e.g., pores, holes, slots, perforations, etc.) may be molded, machined, or drilled into the material of the present invention, for example as shown in FIG. 6A depicting a spinal implant. Channels 630 can be created in any orientation or direction into or through the device 610. Channels 630 may pass completely through the device 610 thereby forming at least one void or reservoir from top to bottom or from side to side, at any angle. The size of the channels 630 can vary or may be the same. It is recognized the compressed pores 620 and channels 630 may provide a structural function and/or biological function. In the example of a spinal implant, the channels 630 may provide a scaffold for vascularization and/or bone ingrowth, in order to facilitate the occurrence of spinal fusion. The channels 630 may also serve to facilitate resorption of the polymer from which the device has been made by reducing the bulk or amount of polymer per device. Additionally, less polymer per device may lead to decreased manufacturing costs, as raw material consumption is reduced. For example, for similar sized objects, one solid polymer and another being 10% porous material prepared as described herein, the porous material utilized 10% less raw material, and may possess markedly better physical characteristics.

With reference to FIGS. 6A & 6B, a channel (e.g., osteoconductive pore) or channels created in the material of the present invention may also be useful for the introduction of various biodegradable materials or matrices 640. For example, material constructed as a spinal fusion implant device 610 may feature a channel or hole 630 that has been filled with material 640. In an embodiment, one material 640 that may be contained in the channel(s) is osteogenic grafting material (e.g., bone grafts, demineralized bone, bone void fillers, hydroxyapatite, bone chips, bioceramics, etc.) to promote bone ingrowth into and through the device 610. The channel 630 may be packed with the osteogenic material, which may be provided in various forms (e.g., chips, strips, sheets, sponges, gels, etc.). Potential biodegradable matrices 640, which may at least partially fill the channel(s), may include beneficial materials (e.g., collagen sponge, collagen-ceramic composites, open-cell polylactic acid (OPLA), etc.). The materials or matrices may act as carriers for bone growth factors or osteogenic proteins, such as naturally or genetically engineered bone morphogenic proteins (i.e., BMP-2, BMP-4, etc.).

In one embodiment of the device, a channel 630 may also be used to accommodate a suitable tool (not shown) to facilitate insertion of device 610 into the living being. For example, in the case of a spinal implant, a tool may be inserted into the channel 630, thereby allowing controlled placement of the spinal implant into a vertebral disc space. The channel 630 and corresponding tool may or may not be threaded, or provide some temporary locking arrangement (e.g., keyed, friction fit, etc.) to provide extra control during implantation, wherein movement of the tool relative to the channel 630 may be limited.

In various embodiments, the compressed porous matrix material 600 can be conveniently machined or molded during compression to form spinal implants with complex geometries and various features. For example, polymer spinal implants may be created in a variety of different configurations (e.g., a horizontal threaded cylinder, a vertical ring, an open box cage, etc.). A gripping means 650 may be provided to ensure adequate stability of the implanted spinal device 610. The gripping means may be any features that prevent the device from sliding or undesirable shifting from the implantation site. These gripping means 650 may operate as a friction fit or incorporate locking elements (e.g., teeth, serrations, ridges, grooves, threads, wedges, blocks, pins, nails, screws, staples, etc.), which may be machined or molded into the device 610. For the example of a spinal fusion implant, the gripping means 650 have the ability to grasp the vertebral endplates and resist lateral movement, thus helping to prevent the implant from migrating out of the vertebral disc space. Additionally, the gripping means 650 may serve to impart increased surface area to the implant device 610, in order to allow the device to withstand spinal pressures. Any recesses created in the gripping means 650 (e.g., the spacing between consecutive teeth or threads) may also serve to facilitate bone ingrowth that may aid in anchoring the device in place. In an embodiment relying on threads functioning as the gripping means 650, the threads may be machined or molded on the outer surfaces of a compressed porous matrix shaped material (e.g., a dowel) to form a device similar to a threaded screw. The threads allow easy and controlled insertion into the vertebral disc space.

In another embodiment, a device 610 may be shaped like a rod (not shown). The rod may feature a gripping means (e.g., ridges or teeth). It is recognized that a device in the shape of a rod may beneficially incorporate a taper, such that one end is larger than the other, or alternatively, the rod may lack a taper.

In another embodiment, as illustrated in FIG. 6A, a spinal cage 610 can be fabricated from the porous matrix material 600 into a spacer in the shape of a wedge. The wedge shaped device 610 may serve to provide vertebral spacing and may aid in interbody fusion between vertebrae. The cage or spacer device 610 may be tapered to provide the correct orientation to the vertebrae with which the device is in contact and can also serve to keep the device in place. It is recognized the spacer may be machined into any other shape or size (e.g., cylindrical, as shown in FIG. 6A, rectangular, kidney shaped, etc.) in order to conform to the shape of the vertebral endplates. Gripping means 650 may be machined into the cage 610 for additional spinal stability. The gripping means 650 may be any height, shape, or size, depending upon the intended use of the device 610. The gripping means 650 may be located on one or more surfaces of the device 610 and oriented in one or more directions on the device 610. As shown in FIG. 6C, the device 610 is sized and configured for engagement between two vertebrae 660. Preferably, the implant device 610 has a height approximately equal to or slightly greater than the height of the intervertebral disc space 670.

In various embodiments, the porous matrix material may be composed of layers or sheets of the same or different types of polymers. Two or more different porous polymer may be included in one device. It is recognized that this invention may be useful for medical devices that require specific abilities, material or mechanical properties, or biological conditions to function optimally in the body. For example, devices may undergo changes in loading over time, require specific degradation rates, may be loaded differently across the surface of the implant, etc. In order to accommodate the special requirements of some devices, in an embodiment, two or more different compressed porous matrix materials may be layered (e.g., stacked on one another, or alternatively side-by-side) to form the device. Alternatively, the same porous matrix material may be compressed under different conditions. In these layered embodiments, the layers of compressed material or materials may possess variable material and structural characteristics (e.g., degradation rates, flexibility, drug delivery rates, etc.). The layers may or may not be fused together. The layers may be compressed by different methods or by different amounts. The layers may provide the device the ability to be multi-functional. For example, it is recognized that one or more layers can perform one function (e.g. provide structurally integrity, maintain shape, etc.) for the device while one or more other layers perform another function (e.g., drug delivery, allow bone ingrowth, etc.). It is also recognized that one or more layers of a multi-layer device may be non-porous so as to provide a device with greater physical integrity.

In another embodiment, the compressed porous matrix material can be machined, punched or molded into any configuration, such as an internal fixation device for use in surgical repair, replacement, or reconstruction of damaged bone in any area of the body. Internal fixation devices may be successfully employed for many conditions and applications (e.g., orthopedic, spinal, maxiofacial, craniofacial, etc.).

Figure 7:
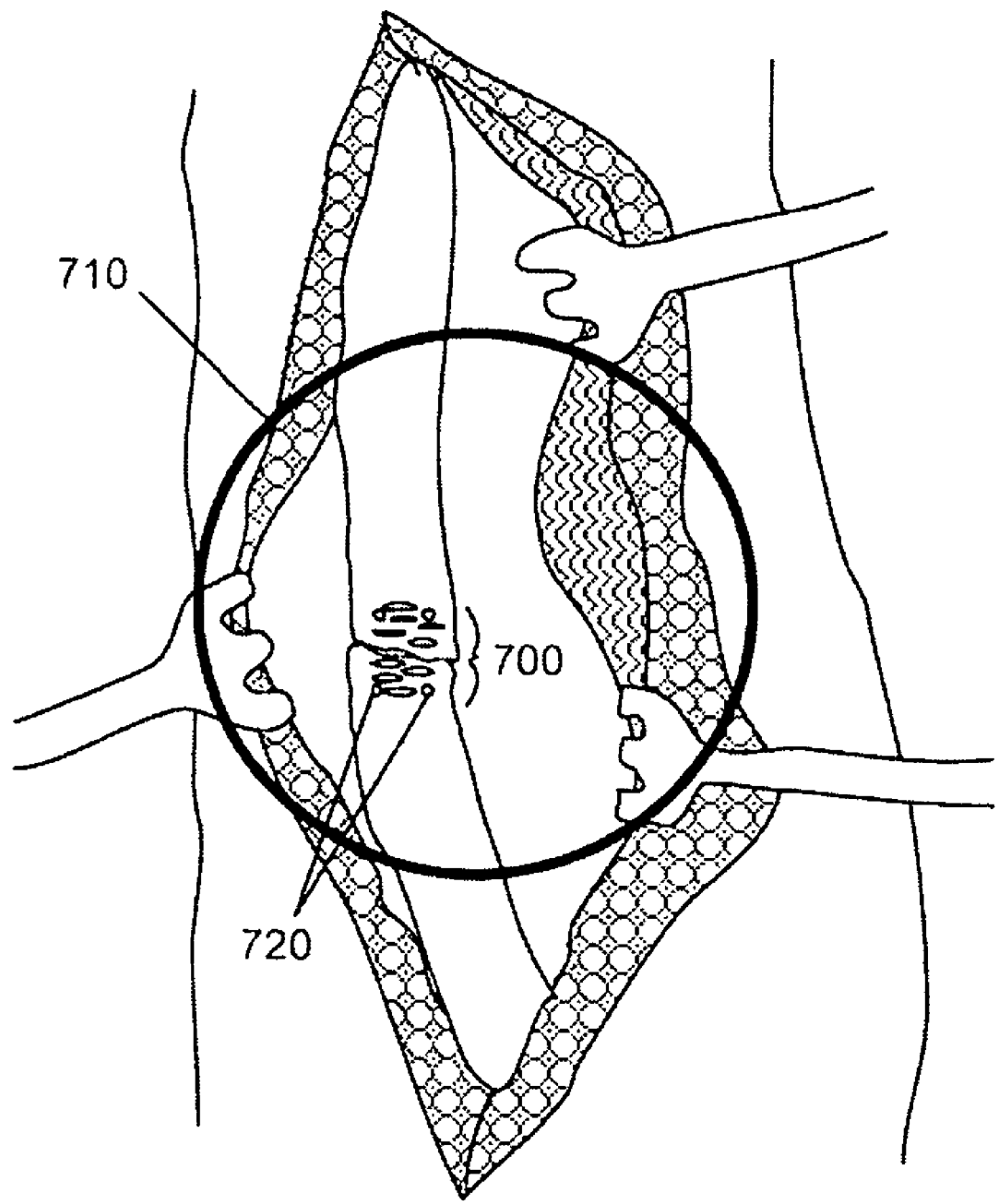
FIG. 7 is a perspective view of an alternative embodiment of the implant and one of the anatomical locations that is suitable for treatment by the implant.

Another possible embodiment of the invention is an internal fixation device, as shown in FIG. 7, where a plate 700, is affixed in an anatomical location 710. A plate 700 may be machined or molded with fixation holes 720 that will allow fixation to bone by various means known in the art (e.g., staples, screws, tacks, etc.). During the surgical implantation procedure, the fixation holes 720 may also be created to fit the anatomical location 710. Holes 720 created contemporaneously with implantation of the plate may allow more accurate placement or fitting of the plate 700, consequently a more effective application of the invention. The plate may be useful as a graft containment device for the repair or reconstruction of defects, such as those caused by surgery, tumors, trauma, implant revisions, infections, and also for joint fusion.

Figures 8A, 8B:
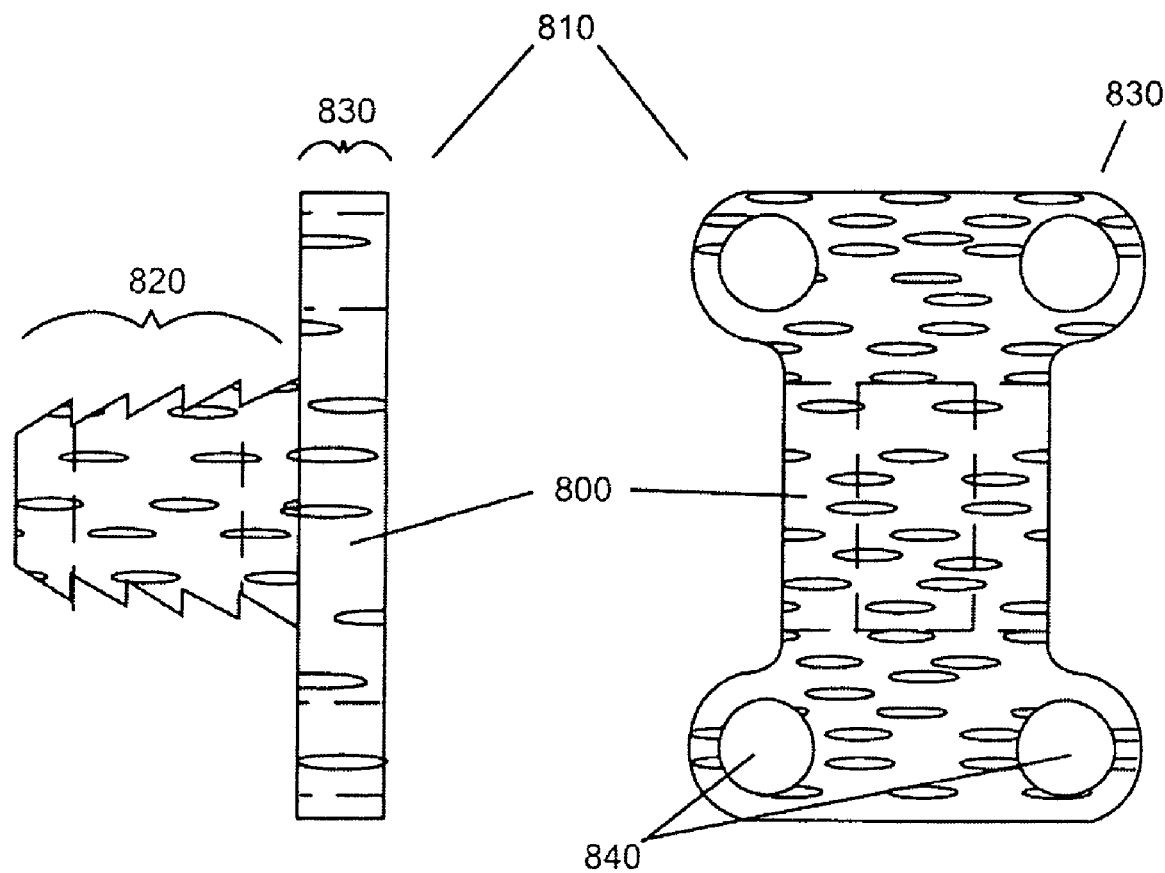
FIG. 8A is a side view of an alternative embodiment of the implant.
FIG. 8B is a front view of the embodiment from FIG. 8A.

In another embodiment, illustrated in FIGS. 8A and 8B, compressed porous matrix material may be machined or molded into an interbody fusion plating system 810, which is a device that is a combination of a cage or spacer 820 and a plate 830. The interbody fusion plating system 810 provides the benefits of a resorbable cage or spacer 820, and further incorporates the advantages of a plate 830. The plate 830 may increase fusion rates by acting as an anterior tension band, reducing motion and movement at the implantation level. The plate 830 will prevent the migration and loosening of the cage 820. The resorption of the plate 830 over time will gradually increase loading on the cage 820 and bony tissue, promoting fusion. The interbody fusion plating system 810 may be fabricated as one solid device or two single devices that can be connected and used together or used separately. The plate 830 may be machined with fixation holes 840 that will allow fixation to bone by means known to those skilled in the art (e.g., staples, screws, tacks, etc.). Alternatively, the fixation holes 840 may be created in the device contemporaneously with implantation, in order to ensure proper placement of the fixation holes in the device.

Figure 9A:
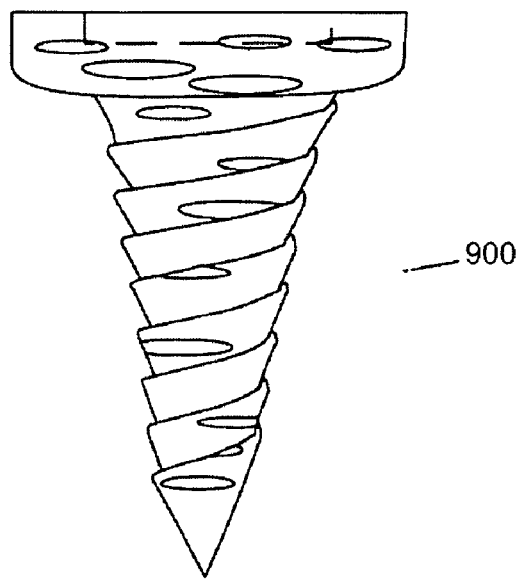
FIG. 9A is a side view of an alternative embodiment of the implant.
Figure 9B:
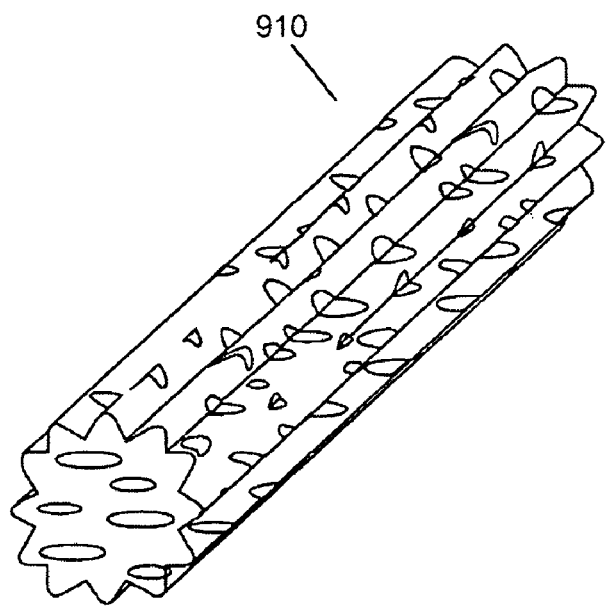
FIG. 9B is a perspective view of an alternative embodiment of the implant.
Figure 9C:
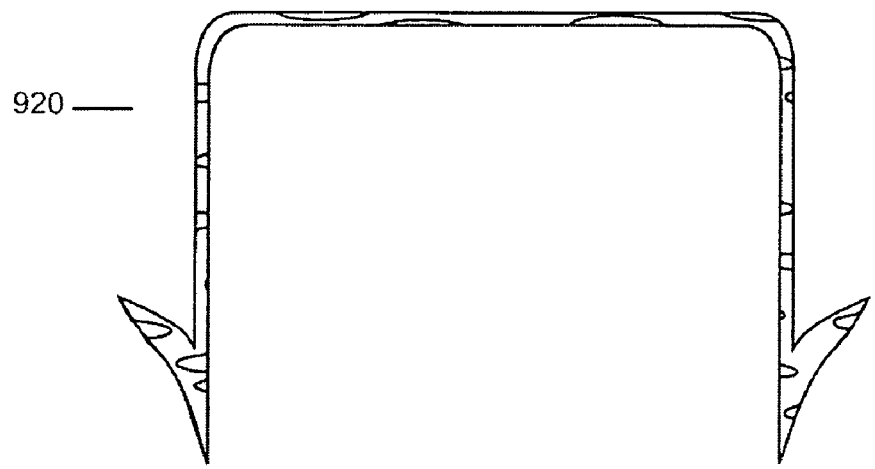
FIG. 9C is a side view of an alternative embodiment of the implant.

Various representative embodiments are illustrated in FIGS. 9A, 9B, and 9C, wherein medical devices may be fabricated into any configuration from the compressed porous matrix material. Such devices may be used in any field wherein the functionality of the porous polymer material as a fixation device may be useful, including but not limited to the fields of internal fixation, trauma repair, sports medicine, etc. For example, these devices suitable for bone and soft tissue fixation may include screws 900, rods, struts, pins 910, tacks, arrows, staples 920, washers, nails, anchors, wraps, tubes etc. These devices may be used in many applications requiring fixation devices, such as the repair of fractured bones.

Although it is envisioned that all of the above embodiments may employ multiple different configurations of porous matrix starting material, (i.e.—porous blocks, porous sheets, porous spheres, porous particulate, etc) for clearer understanding the following embodiments are preferably practiced employing porous particulate and sheet materials. The following embodiments are provided in addition to those above, and not intended to restrict the use of porous matrix particles or sheets as illustrated above.

Figure 10A:
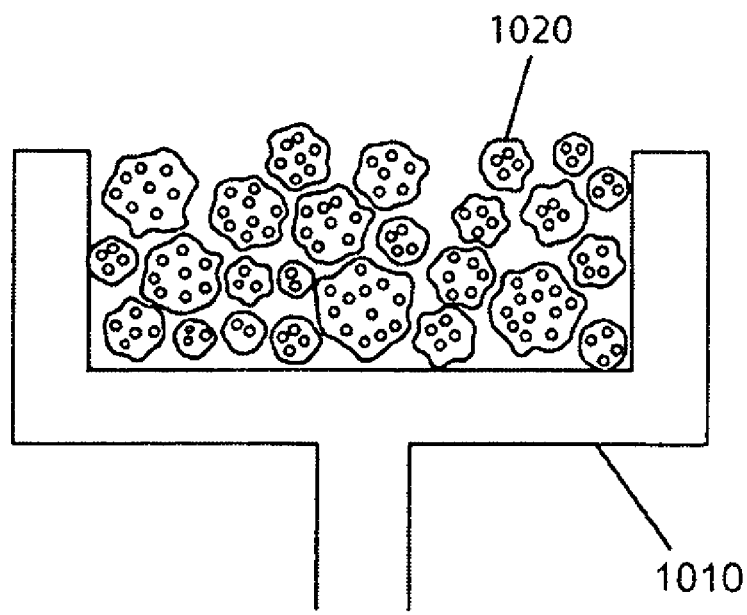
FIG. 10A shows the porous particle matrix material being added to a mold.
Figure 10B:
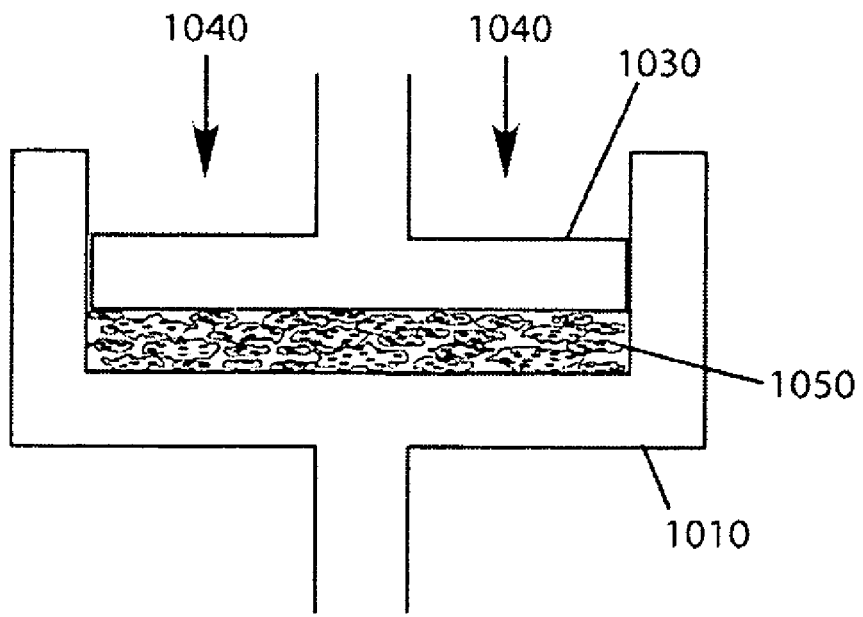
FIG. 10B shows the porous particle matrix material being compressed and sintered.

In another embodiment, and with reference to FIGS. 10A and 10B, porous matrix particles 1020 are provided for creating the final device through a process incorporating at least a sintering step to fuse the porous matrix particles together. The porous matrix particles originally provided for the production of the final product in sintered form may vary in size depending on the particular application, though they will typically have dimensions initially (before sintering and/or compression) ranging, in an embodiment from about 50 to 4000 microns or larger, preferably 250 to 1000 microns, though for alternative uses or embodiments, it is recognized that other sizes may function similarly. In the practice of one method of manufacturing a sintered device, these porous matrix particles are placed into a container or mold 1010, which is preferably heated by means known in the art, and with reference to FIG. 10B, a platen 1030 is then activated to apply compression, as shown by the directional arrows 1040, such that the particles are compressed to a different shape or volume (as shown here by compressed particles 1050). The container or mold 1010 may provide for the finished article in the desired shape, or alternatively may provide an intermediary form, from which the final device is created by further processing (e.g., machining, milling, molding, assembly, etc.). In the described embodiment, the application of compression in combination with sintering leads to the sacrifice of pores (both intrapore and interpore), thereby creating a more dense material having enhanced physical characteristics.

Prior to, during, or after applying compression, the material composed of at least the porous particles 1020 and/or the compressed porous particles 1050, can then be heated above its glass transition temperature to cause a sintering or bonding of the particles (1020 and/or 1050). As with the porous material compression steps described above, if this particulate material, once sintered, is held above its glass transition temperature for a period of time before releasing the compression (e.g. opening the mold), this will allow the molecular chains within the matrix to rotate or move to a lower energy state.

In the practice of this sintering method of forming compressed porous material 1050, it is recognized that by starting with smaller individual porous particles 1020 rather than particles larger in scale, it becomes easier to fabricate a three-dimensional part without requiring secondary machining operations. This is due to the fact that the use of porous matrix in particulate form has benefits over that of solid blocks of porous material in that the porous particles are capable of easily filling irregular topographies that may exist within the surface of the mold or molding platen (not shown). This allows for very detailed construction of surface patterned compressed porous constructs. For example, it may be desirable to fill the mold or container 1010 with porous matrix particles and ensure complete and even distribution, such as by applying vibration to evenly distribute the particles into the deepest recesses of a contoured mold, in order to create highly detailed implants in a single step of compression and sintering, without the need of additional machining. By contrast, larger particulate will be more likely to leave gaps between other particulates, and the container wall, with such gaps making the need for further processing more likely. The constructs manufactured from relatively smaller particulates that are capable of substantially filling the extent of the container are particularly useful in medical applications where protruding or intruding regions are found, as may be required for forming various shapes. For example, the gripping structures, such as those that may be found in spinal spacers as shown in FIG. 6A may be beneficially created through this process. Similarly, zones or cavities can be molded in that are designed to mate up with specialized insertion tools.

In another embodiment (not shown) a solid or porous polymer sheet can be placed above, below or both above and below particles 1020. In this way the particles are fused to the sheet as well as each other. If desired, mold or container 1010 and platen 1030 can have deep cavities (not shown) that prevent isolated points from being exposed to heat thus creating pockets that contain non-fused particles when polymer sheets are placed above and below particles 1020.

Figure 11:
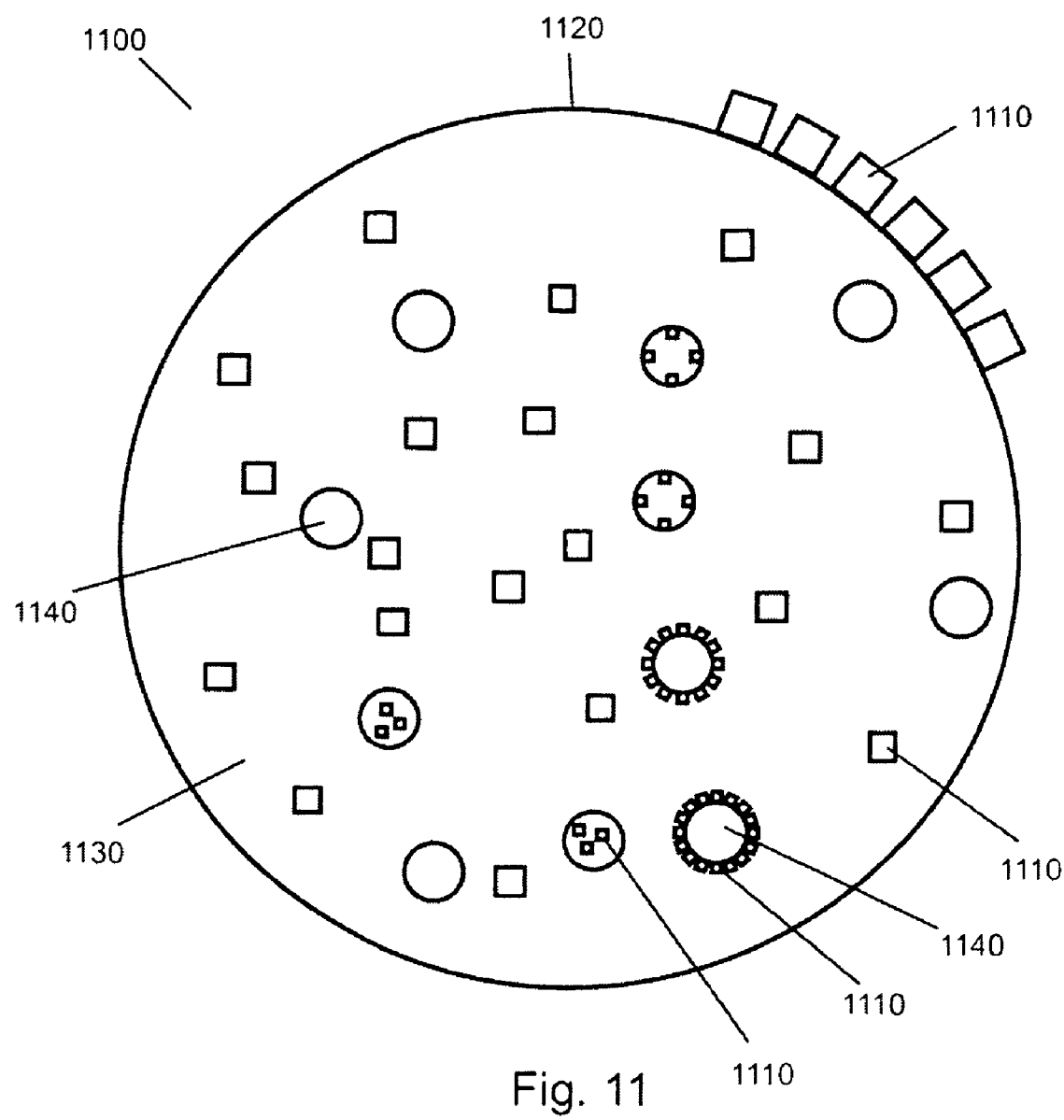
FIG. 11 shows the structure of a porous particle that contains various additive materials.

FIG. 11 illustrates a possible embodiment of a single porous particle 1100, which may be utilized in the manufacture of a sintered device. As depicted here, the porous particle features matrix material 1130, and a plurality of additive components, such as those described in the tables above (e.g., ceramic particles, glass particles, solid polymer particles, metal particles, reinforcing additives, polymer coated particles, filler materials, polymer fibers, collagen, ECM, etc.). It is recognized that the additive components described above may feature a variety of physical properties (e.g., being hydrophobic, hydrophilic, coated with a polymer or drug, etc.). In addition, the porous matrix particle itself (see 1020 of FIG. 10A), either in addition to, or separate from the additive component, may exhibit physical properties of its own, either the same or distinct from those of the additive components. Specifically, porous matrix particles, represented herein by porous particle 1100, as illustrated in FIG. 11 may be created in a common defined shape (e.g., a block, a sphere, etc.) and/or irregular or random shapes and sizes. In an embodiment, the porous particle with the matrix material 1130 may further contain or be coated with at least one additive component 1110. These additives may be associated with only the exterior surface 1120 of the polymer matrix material, rather than extending into the interior of the particulate material, thereby serving as a coating or shell that will become associated with the inter-porosity as will be explained later. It is recognized that particles may be incompletely coated on an exterior surface 1120 by additive component 1110 such that a portion of the exterior surface 1120 is not occluded by additive material. Alternatively, the additive 1110 may be distributed throughout and incorporated into the matrix material 1130 and/or the pores 1140, either in a random or non-random dispersion. In an embodiment of the device having a random dispersion of the additive 1110, the additives may be uniformly distributed throughout the volume of the polymer matrix material 1130. In another embodiment, the additive 1110 may be distributed non-randomly, i.e., having a non-uniform distribution of additive 1110 within the polymer material 1130, or within a depot within the material 1130. The non-uniform distribution may impart a desired quality to the material (e.g., by selectively affecting a portion of the material 1130, by providing the ability to deliver a drug or multiple biologically active agents as a burst and/or over an extended period of time, etc.). In another embodiment, the additive 1110 may be associated with only the pores 1140 within the polymer matrix particle material 1130. In any of the embodiments containing additives, the pores may be open or closed cell, random, or interconnected. Additives 1110 may be in the form of reinforcing agents, biologically active agents, or filler materials, examples of which are found in Tables 2 and 3.

Figure 12A:
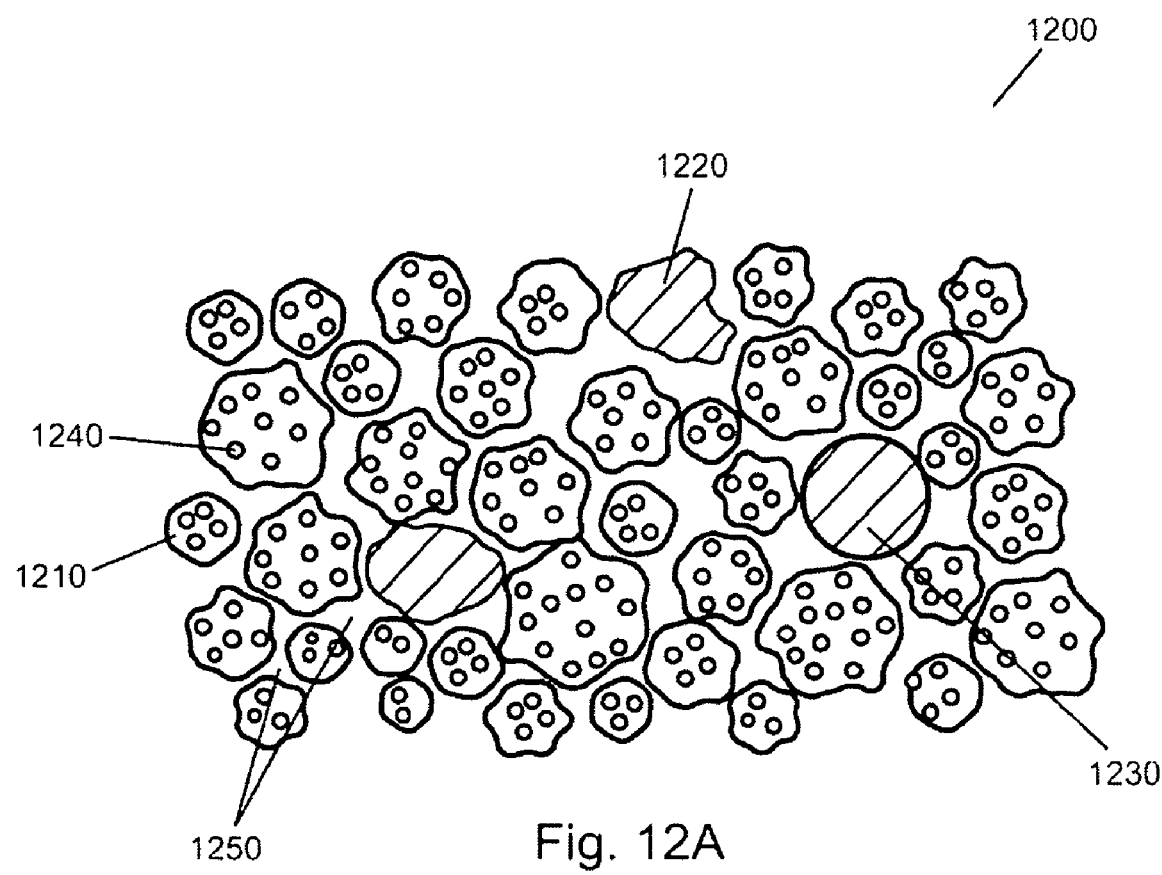
FIG. 12A shows one possible porous particle matrix material before the application of compressing and sintering forces.
Figure 12B:
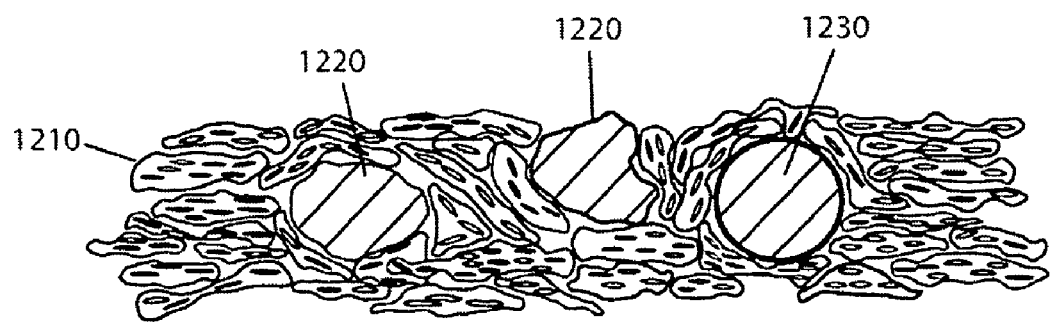
FIG. 12B shows one possible porous particle matrix material after the application of compressing and sintering forces.

A more detailed view of the transformation of porous particle matrix material into a sintered and compressed porous matrix is illustrated in FIGS. 12A and 12B. The various sizes and shapes shown are illustrative and serve to represent the varying types of materials that can be combined and bonded together through a combined compression and sintering process. FIG. 12A depicts a matrix material 1200 prior to compression, composed of porous matrix particles 1210 intermixed with additives, here depicted having non-compressible/compressing resistant filler material 1220 and reinforcing material 1230, here depicted in cross-section as a rod, though other forms of reinforcement are suitable (e.g. screen, mesh, multiple fibers or threads, etc.). A non-compressible or compression resistant material in this context is a material that will not compress substantially as a result of applied compressive forces during processing. For example, if in the production of a device according to the present invention the porous matrix material has greater compressive stiffness than that of the additive material, then glass transition in the matrix should be achieved prior to the compressive step. If the reverse is true and the additive has greater compressive stiffness than the porous matrix, the option to apply the compressive force before or after achieving glass transition is available. It should be noted that monolithic (non-porous) additives composed of identical material as the porous matrix are able to resist compression to a greater degree than the porous matrix and thus can also function as a suitable non-compressive/compressive resistant additive even though they have the same glass-transition temperature. It should also be noted that it might be desirable to have additive materials that deform during the compression step, allowing for greater surface area contact with the porous matrix material. Intrapores 1240 may reside within the boundaries of the matrix particles 1210 and may extend to an outside surface of the particle. Interpores 1250, depicted here as the space existing between particles 1210 and/or additive materials (1220 and 1230) within the construct. During the application of compression and sintering, and as shown in FIG. 12B, porous matrix particles 1210 collapse and fuse together as a result of each application respectively, resulting in a reduction of both intra and inter porosity. Matrix particles 1210 may be forced to conform around non-compressible materials (or even less compressible materials) such as reinforcing material 1230 and filler material 1220 during the compression step. Furthermore, the compression step may result in the compression of the porous particles 1210, and result in the particles conforming to each other, creating a laminated or layered effect as the porous particles and the pores within the porous particles, collapse as a result of the applied pressure. Sintering the porous matrix particles 1210 locks the construct in its final form.

In another embodiment the porous matrix particles may be composed of two or more different polymers. Some of the porous particles may be elastic and have higher glass transition or sintering temperatures. During compression some of these particles may be compressed in their elastic states and then locked in place by other particles that have bonded together but upon the degradation of the bonded particles over time, the more elastic particles may be allowed to return to their original shape.

In another embodiment the porous matrix particles may be composed of two or more different polymers. Some of the porous particles may be rigid and have higher glass transition or sintering temperatures. During compression some of these particles may resist compression and become locked in place, maintaining a more open porosity, by other particles that have bonded together.

In another embodiment the porous matrix particles may encapsulate an additive material in the form of a screen or mesh, rod, thread, fiber, particulate, wherein the matrix particles conform around and through the additive component, locking it into a specific spatial orientation. This process is superior to prior art processing, which would require foaming the polymer around the additive material, with the drawback that due to contraction that occurs during formation, as drying or curing of the foam can distort or warp the additive material into an undesirable shape.

In another embodiment an additive, such as fibers or threads may be intermixed with porous matrix particles in a random or oriented fashion. The compression step locks the fibers into a specific spatial orientation that may be within a single plane or arranged uniformly dispersed throughout the entire volume.

In another embodiment the porous matrix further features a fluid soluble microstructure. This microstructure may be a polymer material, that is arranged within either or both of the interpores or intrapores of the matrix material, and features physical properties that are distinct from the polymer material comprising the particulate component. In the embodiment having a microstructure in the interpore region, the porous matrix particles are entrapped within a polymeric microstructure (e.g. hyaluronan, collagen, etc.) prior to compression and sintering. During the compression step the matrix particles have limited contact with each other creating a discontinuous laminated network, interrupted by the presence of the microstructure. Preferably, the microstructure of this embodiment is fluid soluble, such that as a fluid penetrates (e.g., such as body fluids entering the device upon implantation of the device) into the construct, the microstructure is dissolved and removed, creating a more open structure composed of compressed porous particulate plates.

In another embodiment the microstructure is composed of a rapidly degrading or dissolving material (e.g. a low molecular weight polymer) that binds the porous matrix particles together during the compression step. If the porous matrix particles are elastic they will re-expand as the binder is degraded or dissolved. This may be useful in an embodiment arranged to fill a void within a living being, such that the delivery of a void filler embodiment may occur through a small opening (e.g., by cannulation or injection). If the porous matrix particles are elastic and have been fully compressed, the removal of the binder will release compressed microparticles into the wound site for possible re-expansion once released from the binder.

Figure 13:
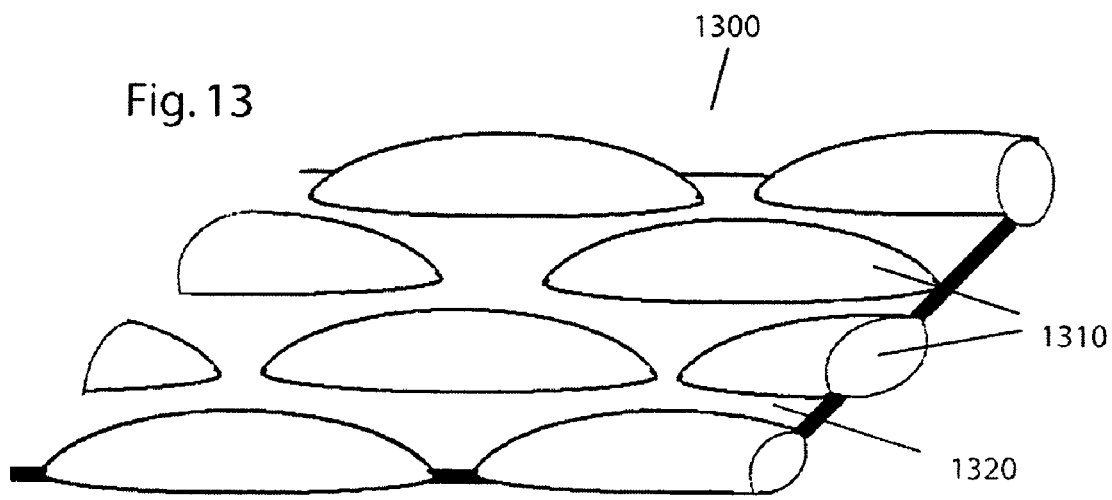
FIG. 13 is a perspective view of one embodiment of a biphasic sheet material.

In another embodiment as shown in FIG. 13, a porous polymer sheet has been compressed to make bi-phasic sheet 1300 having high porosity zones 1310 contained within low porosity zone 1320. The terms "high porosity" and "low porosity" are only meant to be indicative of the relative porosities when comparing one zone with the other zone. For example—the high porosity zone may be 99% porous while the low porosity zone could be any lower porosity, including 98% porous or less. Furthermore the high porosity zone may be 1% while the low porosity zone could be 0%, so long as it is less than the high porosity zone. Conversely, the high porosity zone could be 99% while the low porosity zone could be 0%. When creating a bi-phasic sheet, one may utilize elastic polymers, such as polycaprolactone and polycaprolactone/polylactic acid copolymers. In this way, the high porosity zones are able to elongate along with the low porosity zones, without separation of the two phases, as the biphasic sheet is physically manipulated, such as stretching, as the phases will move or react together, rather than having one phase separate or fail before the other. Although it is also conceived that non-elastic polymers could be desirable in surgical applications wherein elongation is not anticipated or wanted. It is desirable that at least the high porosity zones are hydrophilic and capable of adsorbing biologically active agents, such as blood and bone marrow aspirate, as well as liquids containing other biologically active agents, such as those listed in table 2. This can be accomplished by use of surfactants or naturally hydrophilic materials in the implant's construction.

Figure 14A:
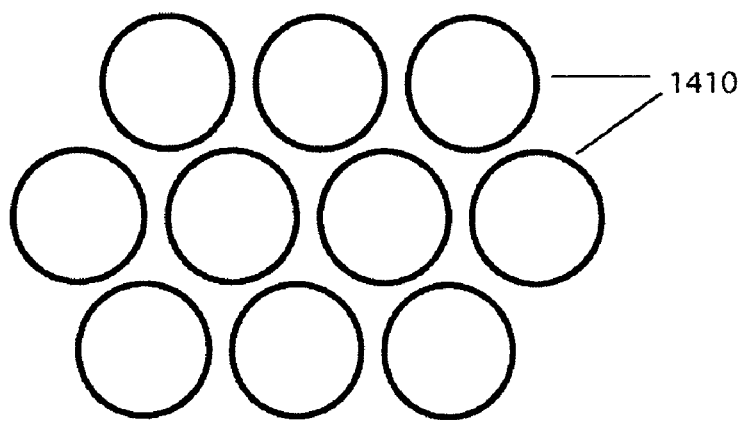
FIGS. 14A and B illustrate two possible patterns for high porosity zones on a biphasic sheet embodiment.
Figure 14B:
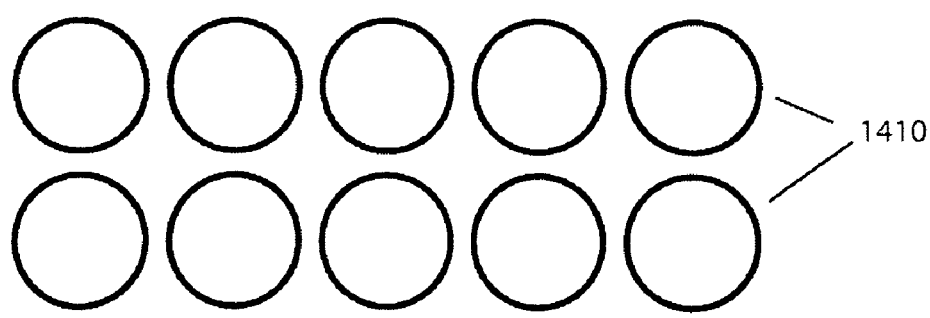
FIG. 14C illustrates a variety of possible profiles for high porosity zones on a biphasic sheet embodiment.
Figure 14C:
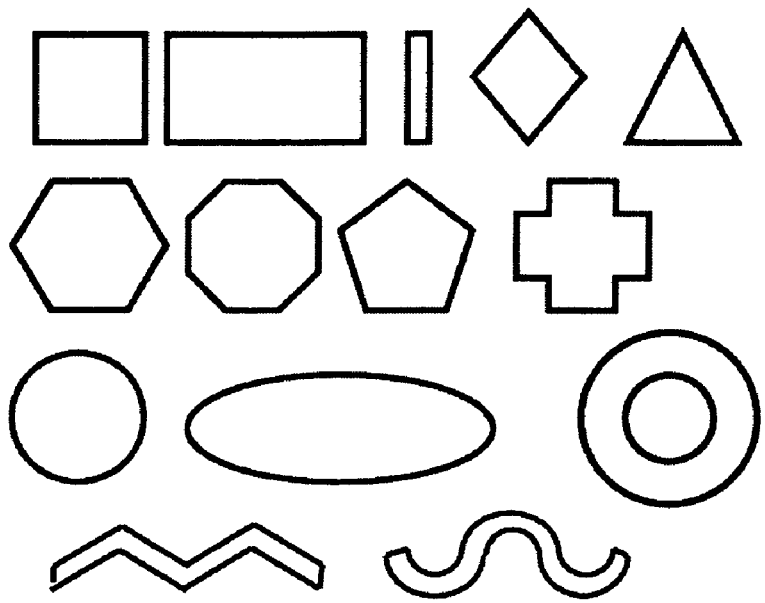

Arrangement of the high porosity zones within the low porosity zone can be organized or random and spacing between the high porosity zones can be tailored to meet aesthetic, biologic, or mechanical needs. FIGS. 14A and 14B represents two different simple arrangements of high porosity zones 1410 in the form of simple circles. The high porosity zones can take on a variety of geometric shapes, examples of which can are shown in FIG. 14C. Additionally, the high porosity zones can take on less regular or random shapes. The high porosity zones can also appear as repeating or random patterns, shapes, numbers, letters, logos, or figures, such as birds and flowers, allowing for easy identification or product branding.

Figure 15:
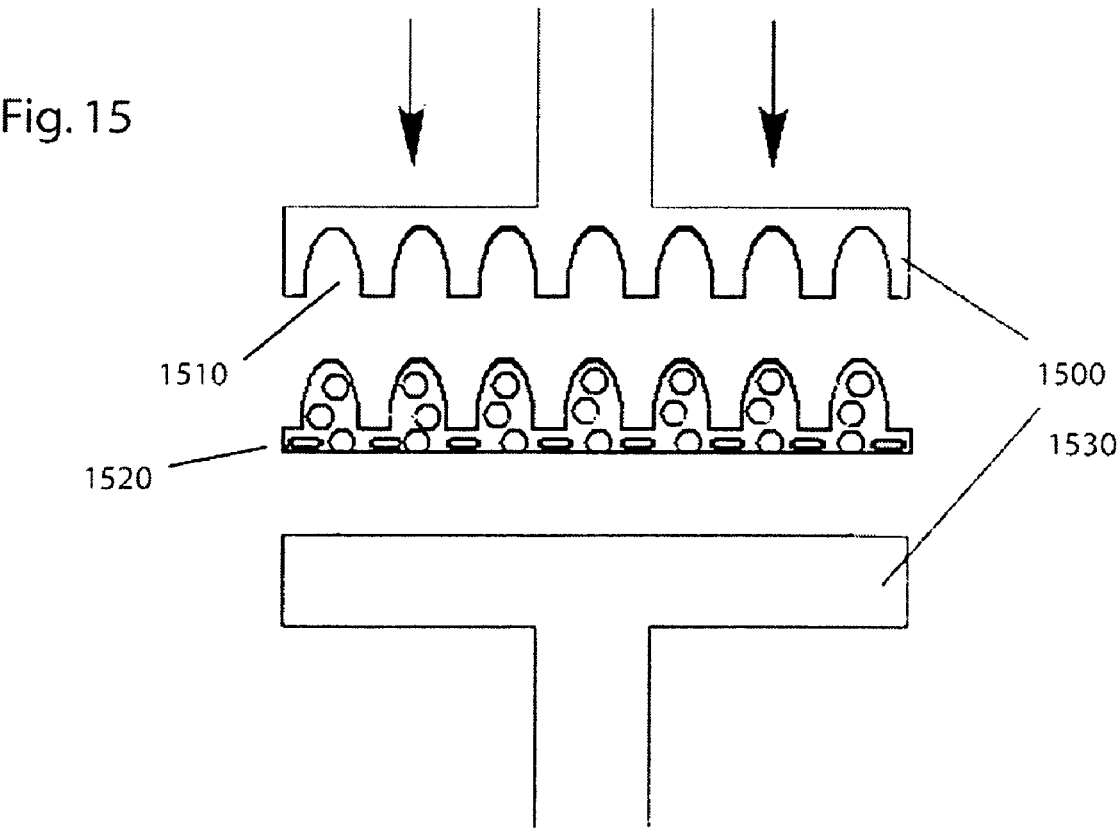
FIG. 15 shows the biphasic device produced by being compressed by a pair of plates, where the upper plate features at least one cavity.

Creation of a biphasic reinforcement sheet can be accomplished as depicted in FIG. 15. In this depiction, upper platen 1500 containing cavities 1510 has just completed its compression cycle to produce biphasic reinforcement sheet 1520. When heat is used as part of the fabrication process it is desirable to have it applied through lower platen 1530 in order to protect the high porosity zones. Heat may optionally be applied via the upper platen if the high porosity zones are also being compressed, but to a lesser extent than the low porosity zone. Another option is to have the cavities in the upper platen 1500 be deeper than the thickness of the starting porous material, so that the high porosity zone of the reinforcement sheet has little or no contact with the heated platen.

Figure 16A:
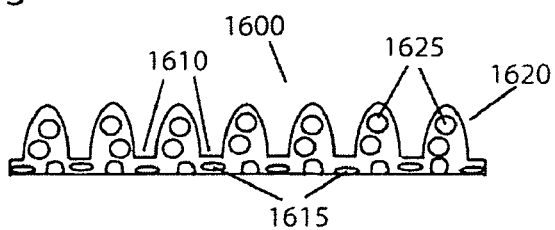
FIGS. 16A, B and C depict a biphasic device formed by compression of a single porous sheet material between platens having cavities, where the compressed low porosity zone retains at least some level of porosity.
Figure 16B:
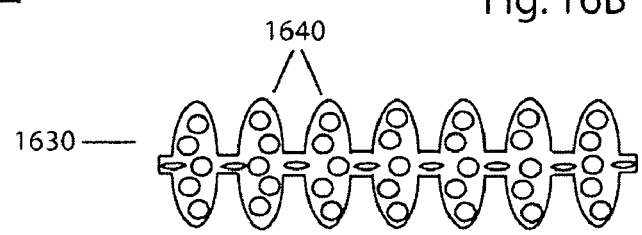
Figure 16C:
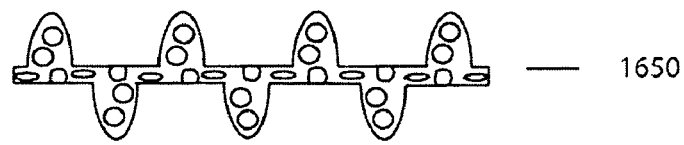

Through the incorporation of cavities into one or both of the platens 1500 or 1530, a variety of different shaped materials may be manufactured. FIG. 16A shows a cross-section of biphasic reinforcement sheet 1600 having low porosity zone 1610 having collapsed pores 1615 surrounding high porosity zone 1620 having minimally or non-collapsed pores 1625. In another embodiment, FIG. 16B shows biphasic reinforcement sheet 1630 wherein the compression plates or platen used during fabrication each have cavities directly across from each other, thus producing high porosity zone 1640 that transverses the thickness of the sheet. FIG. 16C shows another embodiment, wherein the cavities on the upper compression plate or platen used to produce biphasic reinforcement sheet 1650 are not aligned with the cavities in the lower compression plate or platen.

Figure 17A:
FIGS. 17A, B and C depict a biphasic device formed by compression of a single porous sheet material between platens having cavities, where at least a portion of the porous sheet material has been compressed to an extent where the polymer has fused, and no porosity remains.
Figure 17B:
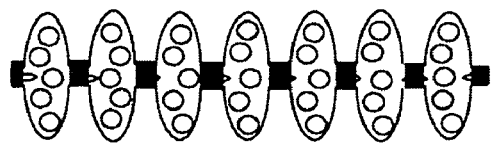
Figure 17C:
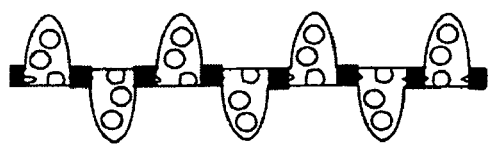

FIGS. 17A, 17B and 17C show comparable biphasic reinforcement sheets to those depicted in FIGS. 16A, 16B and 16C, with the exception that the regions that have been highly compressed by the platens have been fused to the point of having zero percent porosity, or very near zero. In this manner, a biphasic sheet can be made that functions as a polymer mesh or web arranged as a sheet, and having interspersed in the openings of the mesh regions of high porosity fused to the sheet. In this manner, the compressed biphasic material is able to provide both the benefits of a porous sheet material with large areas of high porosity, and the mechanical strength benefits comparable to that of known polymer mesh materials, as the biphasic device provides both highly compressed regions along with the high porosity regions. In order to prevent accidental collapse of the high porosity zone, one may heat the plates or platens to temperatures insufficient to melt or result in flow of the polymer when not under compressive force. Under high compressive force, the polymer is capable of flowing, thus if sufficient time is allowed, the porous structure will collapse and flow creating a homogenous compression molded sheet that surrounds minimally impacted porous islands that are isolated from the compressive force by virtue of their presence within the cavities of the platen or plate.

Figure 18A:
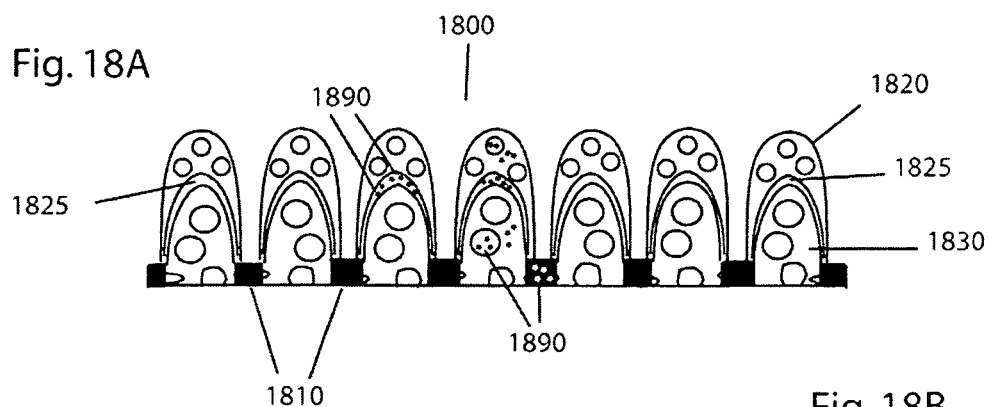
FIGS. 18A and 18B depict a biphasic device formed by compression of two porous sheet materials between heated platens having cavities, where in the unfused regions, a contained space is created.

In another embodiment depicted in FIG. 18A, two separate porous sheets were layered together and placed within a compressive tool as depicted in FIG. 15, though it is recognized that the same effect may be accomplished by simply doubling over a larger sheet of porous material that may be placed within the platens. The two sheets were compressed together in the presence of heat and allowed to sit until bonded together creating duel layered biphasic reinforcement sheet 1800. Bonding of the two original sheets is limited to low porosity zone 1810, thereby creating a zone of high density. High porosity zones are protected from heat and thus create upper high porosity zone 1820 and lower high porosity zone 1830 separated by contained space 1825. Notice how this process results in contained space 1825 existing above the plane of low porosity zone 1810. As contained space 1825 can serve as an origin point for delamination, one may place the low porosity zone 1810 under sufficient heat, pressure and time to allow polymer to flow across the gap, which allows the distinction between the original two sheets to at least partially collapse, and eliminating the potential delamination failure mode. As a result of this process, the porosity in the low porosity zone 1810 may or may not collapse to zero. This area of flow allows the polymer materials to fuse, thus creating a high density zone.

Figure 18B:
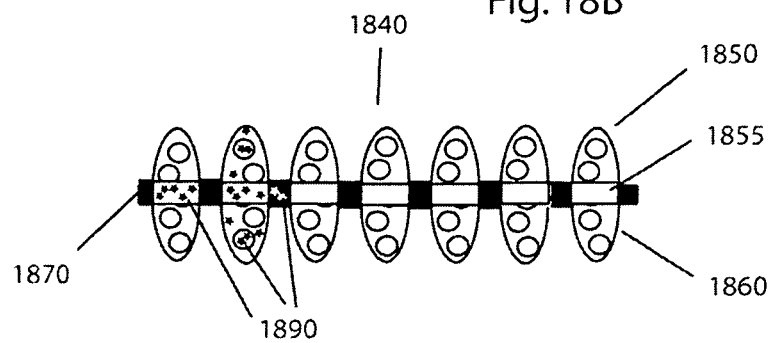

The embodiment shown in FIG. 18B is the result of two separate porous sheets being layered together and compressed together in the presence of heat as described above for FIG. 18A with the difference being that the bottom platen or plate also had cavities aligned directly across from the cavities in the upper plate. In this way duel layered biphasic reinforcement sheet 1840 is created with upper high porosity zone 1850 and lower high porosity zone 1860 separated by contained space 1855 wherein contained space 1855 is centered within the plane of low porosity zone 1870.

Figure 19A:
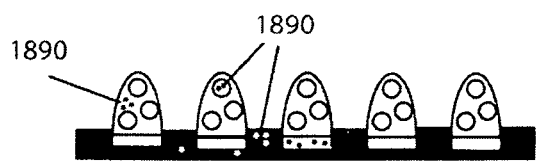
FIGS. 19A and B depict a biphasic device formed by compression of a single porous sheet material and a non-porous sheet material, between heated platens having cavities, where in the unfused regions a contained space is created.
Figure 19B:
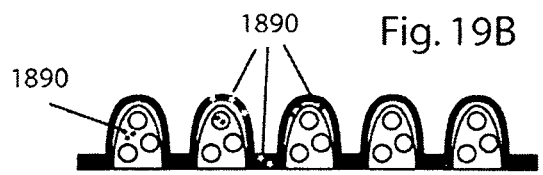
FIG. 19C depicts a biphasic device formed by compression of a multiple porous sheet materials of different sizes arranged in a step-like structure, between heated platens having cavities, where in the unfused regions having multiple layers, at least one contained space is created.

If desired a non-porous or solid sheet could be substituted for one of the porous sheet layers in either 18A or 18B, in order to create a solid barrier along one surface, as depicted in FIGS. 19A and 19B. In FIG. 19A, a porous sheet was layered onto a non-porous sheet, and compressed as described previously, thereby creating a non-porous surface along the bottom, with the high porosity region having been compressed by the platen with the cavities, to form areas that remain free of compression and remain porous, and areas that have fused with the lower, non-porous layer, with the porosity having been sacrificed. Alternatively, as shown in FIG. 19B, the porous layer may be underneath the non-porous sheet, and as the compression is applied, the non-porous sheet will conform to the platen with the cavities, but elsewhere will fuse with the polymer layer underneath. In either the case of FIG. 19A or 19B, the regions with the cavities of the platen will not be compressed, or fused, and will result in a contained space 1925 or 1945 between the two layers. As before, the additive 1890 may be incorporated into the contained space, or the polymer layers.

Figure 19C:
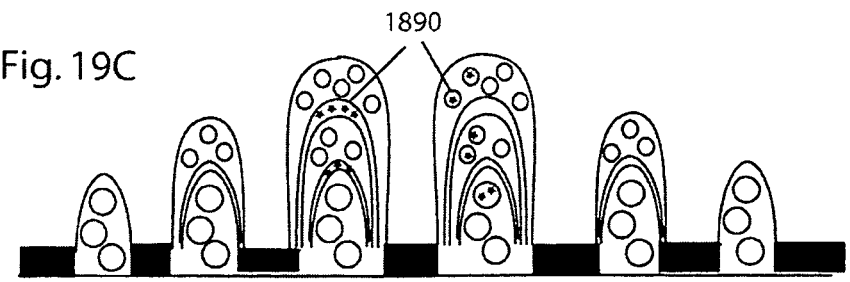

Additionally, more than two sheets can be layered together, as can be seen in FIG. 19C. In this manner, one may produce a biphasic sheet with multiple contained spaces between each of the layers in the discrete high porosity regions. In another embodiment additional layers can stacked up such that the layers serially become smaller, larger or both, in order to create a bonded structure having a step-like structure, as depicted in FIG. 19C. For example, a 2 inch square porous sheet can be covered with a 4 inch square porous sheet that can be covered with a 6 inch square porous sheet and so on. After compression and fusion a biphasic sheet having an outer parameter composed of a single layer surrounding a middle double layer and a center triple layer is formed.

As described previously concerning FIGS. 5A to 5D, additive materials such as biologically active agents, reinforcing materials, particulate and filler materials (see tables 2 and 3) can be incorporated into, or onto, one or more of the separate sheets prior to their being bonded together. In another embodiment these same additive 1890 can be separately placed between one or more layers wherein compression and heat are used to lock the additive materials in place. This process allows for a unique relationship between the bonded sheets and the additive materials. Again with reference to FIGS. 18A and 18B, and 19A, 19B, and 19C, additive materials 1890 that fall within low porosity zones 1810 or 1870 will become encased and restrained within the matrix making up these zones. Additives that fall within spaces 1825 or 1855, although surrounded, will remain distinct and separate from the sheets that have been bonded together, thereby creating isolated pockets or physically constrained pockets with the additive materials.

The additive 1890 may serve to further reinforce biphasic reinforcement sheet 1800 or 1840. The reinforcing additives may serve to enhance the characteristics of the sheet, such as mechanical strength (e.g., modulus of elasticity, compressive strength, tensile strength, etc.) and biodurability (e.g., hydrolytic degradation, strength retention, etc.). To further improve the mechanical properties of the sheet, the reinforcing elements may be interwoven, layered, or compacted together during compression and bonding of the biophasic sheet. If the reinforcement elements are strengthened in one direction, then these elements can be layered and oriented 90 degrees to each other in order to achieve isotropic properties in the finished material.

When the additives are arranged to serve a biologic property, the two zones of the biphasic reinforcement sheet can serve to create a bimodal release profile with the additives located within contained space 1825 or 1855 being immediately available, while additives located within low porosity zones 1810 and 1870 remain sequestered away. It is also contemplated that additives may exist primarily within either the low porosity zone, or the space located between the two high porosity zones, while the other area is essentially free of the additives.

It will be obvious to those skilled in the art that porous blocks, porous sheets and porous matrix particles can be compressed and sintered together in multiple configurations to create unique laminate structures. These laminations may be composed of identical or dissimilar polymers and fillers or reinforcing material may be located within or between the laminations. It will also be obvious to those skilled in the art that blocks, sheets and particles can be combined in order to create unique structures, such as having porous matrix particles and porous matrix sheets being compressed and sintered to form a single matrix.

The following examples are given for purposes of illustration to aid in understanding the invention and it is to be understood that the invention is not restricted to the particular conditions, proportions, and/or methods set forth therein.

EXAMPLE 1

The objective of this example is to compare the physical properties of different Poly-1-lactide (PLA) porous matrix materials after being compressed 0, 40, 60, and 80% of its original height. Static axial compression tests were performed to measure the maximum compressive loads of the porous matrix materials after being compressed to different percentages of their original height. The compression tests will demonstrate the compressed material's mechanical properties can be altered and controlled over a wide range of possible values. The final properties of the compressed material are determined by the properties of the starting material and the amount of compression used. The final product is a material that has tensile and compressive strengths similar to that of non-porous polymer yet is not as stiff or subject to failure by cracking as non-porous polymer. Mechanical and porosity tests will assure a device fabricated from compressed porous matrix material (e.g., a spinal interbody fusion device) is able maintain its porosity and absorb fluids, while still being able to withstand large stresses and loads it may be subjected to (e.g., the maximum physiologic loading expected in the lumbar spine of a human being of at least 10,000 N, or roughly 85 MPa).

The compression test procedure for the compressed porous matrix materials are based on ASTM standards D1621-94, Standard Test Method for Compressive Properties of Rigid Cellular Plastics, and D1667-97, Standard Specification for Flexible Cellular Materials—Vinyl Chloride Polymers and Copolymers (Closed-Cell Foam). The only polymer used for this example was Poly-l-lactide (PLA). The porous matrix materials were produced by methods known to those skilled in the art. The porous matrix materials can be created with porosities that initially range from 98% to 86% or lower. At least five cylindrical specimens (15 mm in diameter and 15 mm in height) were machined from each material. An axial load was applied via a materials testing system to each cylindrical specimen at a rate of 12.5 mm/min until a stopping point of 50% strain. Load versus displacement curves were measured and recorded. For each test, the maximum compressive load and compressive modulus of elasticity were calculated and recorded.

Additional material property tests included porosity and wettability. The wettability and porosity were measured to determine the effects of compression on the porous material. The porosity of each material was measured before and after being compressed using a Helium Pycnometer, which determines the density and volume of a sample by measuring the pressure change of helium in a calibrated volume. The wettability (ability of the material to absorb fluids) of the material was determined on a pass/fail basis after compression, subjectively assessing the ability of the porous material to absorb fluids.

The different PLA materials with initial porosities ranging from 97% to 86% were compressed by 0% to 84% of their original heights. Up to the maximum compression of 84%, the materials maintained their wettability and a percentage of the original pre-compressed porosity. The material's strength after compression was directly related to the initial porosity and amount of compression. For example, the initial porosity and compression strength of the uncompressed materials ranged from 97% porosity with 30 N of compressive strength to 86% porosity with 624 N of compressive strength. At 40% compression, the strength and new porosity for the two materials with the lowest and highest initial porosities ranged from 67 N and 94% porosity (97% initial porosity) to 1348 N and 75% porosity (86% initial porosity). The compressive strength and porosity ranged from 101 N and 90% (97% initial porosity) to 2249 N and 71% (86% initial porosity) after 60% compression. The final compression set point of 80% resulted in compressive strengths and porosities ranging from 326 N and 84% (97% initial porosity) to 4889 N and 57% (86% initial porosity).

In order to find a compressive strength greater than 10,000 N, the material with the lowest initial porosity (86%) was compressed by 84% of its original height. At the 84% compression, the maximum compressive load was 12,985 N and the actual measured porosity was 41%. Relying on the following equation, where theoretical porosity can be calculated as 1-[(1-initial % porosity)/(1-% compression)], the theoretically calculated porosity would have been around 13%, with the difference between the theoretical and actual porosity percentage values most likely being due to the sample not being restrained as compression was applied, and allowed to expand horizontally beyond the 15 mm diameter of the original sample. Had there been some restraint against expansion while being compressed, the percentage porosity would have been reduced to less than 14% porosity, down from the original 86% of the initial material. The maximum compressive load of 12,985 N is above the maximum expected physiological spinal loading of 10,000 N. The porous matrix material can be produced with a lower initial porosity and compressed by various methods (previously described) to increase the maximum compressive strength, providing a significant safety factor compared to both typical and maximum physiological spinal loading.

The results from the porosity, wettability, and compression tests prove that PLA porous matrix material can be compressed by various degrees to give a wide range of compressive strengths while still maintaining its porosity. By altering PLA porous material and the amount of compression, any amount of porosity and compressive strength may be created. The compressive strengths were found to range from 30 to almost 13,000 N. The compressed material may be useful as an internal fixation device, such as a spinal fusion cage. A spinal fusion cage made of compressed porous matrix material would be able to withstand the maximum physiologic loading expected in the lumbar spine of at least 10,000 N. The maximum compressive load found in this example of 12,985 N is above the maximum physiological spinal loading for a lumbar disc. Even accounting for the horizontal expansion during compression, the increased area that results is less than the surface area of a lumbar vertebra and thus still exceeds the expected load. The porous matrix material can be produced with a lower initial porosity and compressed by various methods (previously described) to increase the maximum compressive load providing a significant safety factor compared to both typical and maximum physiological spinal loading.

EXAMPLE 2

While Example 1 demonstrated that PLA porous matrix materials could be compressed, this example serves to illustrate that porous matrix materials made of different polymers can also be compressed and will compare the physical properties of the two compressed materials. Polylactide/Poly ϵ-Caprolactone (PLA/PCL) and Poly(desaminotyrosyl-tyrosine ethyl carbonate) (PDTE) Carbonate were used to create two different porous matrix materials. The compression, porosity, and wettability tests described in Example 1 were used to test these materials.

Static axial compression, wettability, and porosity tests were conducted as described in EXAMPLE 1.

Before compression, the porosities of the PLA/PCL and PDTE Carbonate were 92% and 94%, respectively. Up to 40% compression, the materials show little to no change in porosity. At 80% compression, the more brittle porous material (PDTE Carbonate) had a porosity of 73% compared to 66% porosity for the PLA/PCL material. It should be noted that, as in EXAMPLE 1, the samples were not restrained from expanding horizontally during compression; therefore the actual measured porosity values are slightly different from theoretically calculated porosity values.

The maximum compressive strength results showed significant differences in the mechanical strength of the compressed materials. At 80% compression, the PDTE Carbonate had a maximum compressive strength greater than 1500 N compared to a compressive strength of 450 N for the PLA/PCL material. At 87% compression, the PLA/PCL with 59% porosity was able to withstand a maximum compressive load of 581 N.

The objectives of this study were to determine if different materials (other than PLA) could be compressed and to compare the material and mechanical properties of two different porous matrix materials (PLA/PCL and PDTE Carbonate) after being compressed different percentages of their original height. Due to the elasticity of the PLA/PCL material, it would only hold its shape if compressed at temperatures near its glass transition temperature. The PDTE Carbonate could be compressed with or without heat and hold its compressed shape. After compression, each material still retained a high percent of its porosity and was able to absorb fluids. The compressive strength results from the compressive tests were significantly different for each material. The PLA/PCL material had a compressive strength much less than the PDTE Carbonate material. The elasticity of the PLA/PCL material prevents it from being a material able to withstand large compressive loads. This study proves that it is possible to compress elastic and brittle materials, as well as non-lactide materials.

EXAMPLE 3

The objective of this example is to report on the results of tests completed on simulated cervical spine spacers. Porous polymer particles, ranging from about 50 microns to about 800 microns, composed of 70/30 L-D,L Lactide purchased from Boehringer Ingelheim, with a glass transition of approximately 50 degrees centigrade, were weighed and poured into a mold in the shape of the desired cervical spacer. The mold had the following dimensions: 13 mm O.D.×5 mm I.D.×7 mm in length. Vibration was used to ensure that the particles fully filled the cavity. After compressing this material to the proper dimension, the mold was placed in an oven at 80° C. and allowed to sinter for 2 hours. Once the mold cooled, the spacers were removed, dimensionally measured and weighed. Samples produced had final porosities of approximately 34%, 42% and 50%. The samples were then compression tested utilizing a Lloyd Tensile Tester, Model LR30K. Values at 2% offset yield showed a consistent correlation between density and compressive stiffness. This testing showed that compressing and sintering the porous polymer particles down to an average porosity of 34% can yield a material that can withstand compressive loads of over 2000 Newtons or roughly 17 Megapascal (MPa). At these values, this material and process could be utilized for the fabrication of cervical spine spacers, particularly in human patients.

Biphasic Reinforcement Sheet Examples

EXAMPLE 4

Preparation of Single Layer Sheet

Starting with a sheet of 70/30 PLLA/PCL Porous Tissue Matrix™, a rectangular piece was cut to a size of approximately 4"×5". Using a Carver Hydraulic Press, model number 3895.4DI0A00, with heated platens, the temperature controllers were set to 131° F. and allowed to stabilize for 15 minutes. The press was placed in the "Manual" mode and the "Force" value was set to 56000 pounds. The "Pump" value was set to 70%. Two 0.50-inch thick aluminum plates that were keyed together and coated with PTFE were used to transfer heat to the material being compressed. A patterned press plate 0.060 inches thick and containing 0.187 inch diameter holes on a staggered 0.25 inch center to center spacing was inserted on the top surface of the bottom aluminum plate. The rectangular sheet of PTM material measuring approximately 0.85 mm in thickness was then placed on top of the patterned press plate and the top aluminum plate was laid on top of the PTM sheet and keyed to the lower plate. This laminated pressing fixture was then placed into the Carver Press and the moving lower platen was activated. Pressure and heat were maintained for approximately one hour. The lower platen was then released and the fixture was removed from the press and opened to remove the patterned sheet. The final sheet consisted of areas of porous circles and clear sections that interconnected in between, and surrounded these circles (as depicted in FIG. 13). The thickness of the clear sections measured 0.11 mm and the thickness of the porous circles measured 0.85 mm. A wetability test demonstrated that the porous circles instantly wet when exposed to fluid.

EXAMPLE 5

Preparation of Double Layer Sheet

Starting with two sheets of 70/30 PLLA/PCL Porous Tissue Matrix™, rectangular pieces were cut to a size of approximately 4"×5". As in Example 4, the starting sheet material thickness was approximately 0.85 mm. Using the same equipment as in Example 1, the sheets were stacked on top of each other and 0.008-inch shims were placed around the edges on top of the patterned press plate. These shims were used to ensure the compressed regions had a controlled minimum material thickness. After compression was applied to the dual layer sheet, in the manner described in example 4, the resultant material contained the same visual characteristics as the compressed single layer sheet, with the notable addition of pockets between the two layers occurring inside of the porous circles, creating contained spaces described above. The thickness of the clear sections after pressing measured 0.22 mm and the thickness of the porous circles measured 1.46-1.53 mm.

EXAMPLE 6

Tensile Strength Comparison

Four different PLLA/PCL sheet configurations were tested to compare tensile strength values. The first configuration was a foamed PLLA/PCL PTM material. The second configuration was compressed PLLA/PCL PTM material that was visually clear thereby indicating that it contained no porosity. The third configuration or sheet was a single layer sheet of Biphasic Reinforced material, as created in example 4. Finally, the fourth sheet was a double-layered sheet of Biphasic Reinforced material, as created in example 5. Test strips were prepared by cutting the sheets to be tested to obtain strips that measured approximately 2 centimeters in width by 76 millimeters in length. Using a Lloyd Tensile Tester, Model No. LR30K and fitted with a 1 KN load cell and GF-9 Testing Grips, the test strips were loaded into the grips and pulled to failure. The test was run at an extension speed of 50 mm/minute and the initial gap between grippers was set at 25 millimeters. Test strips were measured for width prior to initiating testing. The maximum tensile values were then divided by the measured widths of the test strips in order to determine maximum tensile strengths per centimeter of width. These resultant values were then averaged and plotted on the bar graph depicted in FIG. 20 to compare the tensile strengths of the four configurations.

Figure 20:
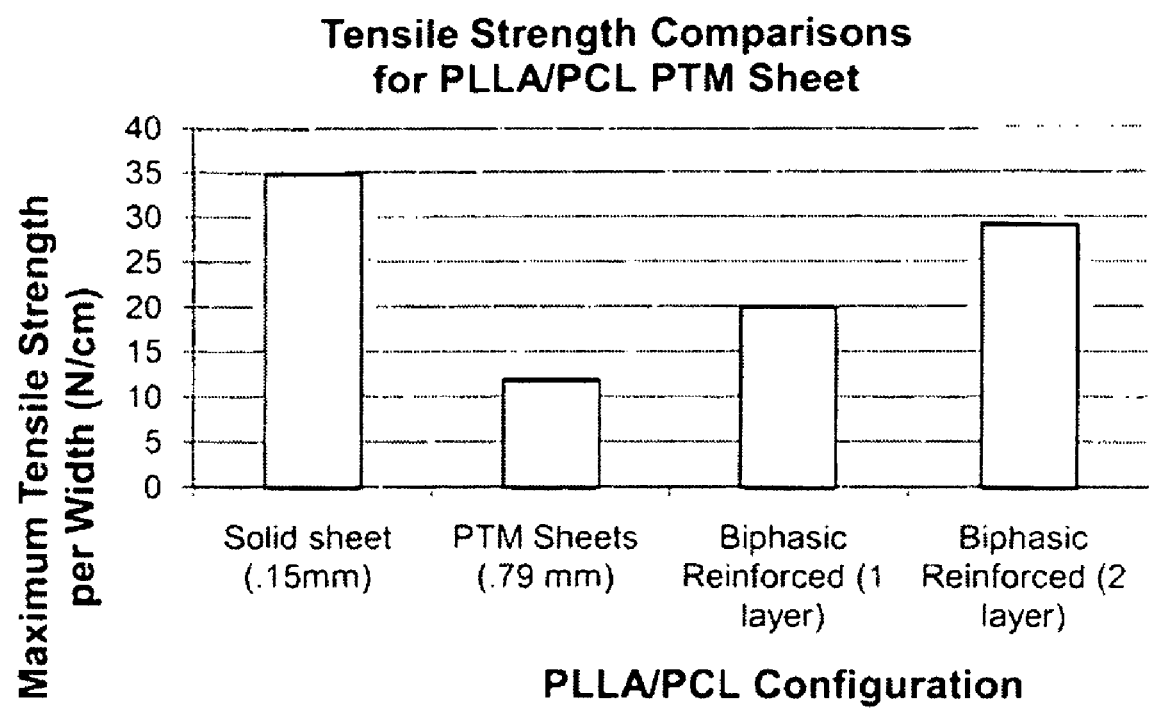
FIG. 20 depicts a comparison of the tensile strengths of four configurations.

As shown in the bar graph in FIG. 20, the solid sheet configuration had the highest tensile strength per centimeter width. The two-layered Biphasic Reinforced sheet configuration, the single layer Biphasic Reinforced sheet, and then the foamed PTM sheet followed in that order.

As would be expected, the solid sheet is the strongest since it is a solid structure. In comparing the PTM sheet with the Biphasic Reinforced 1-layer sheet, the reinforced sheet is 1.68 times stronger due to the reinforcing effects of the clear sections on the material. In comparing the Biphasic 1-layer and 2-layer sheets, the 2-layer sheet is approximately 1.5 times stronger then the 1-layer material. These results indicate that the tensile properties of these sheet configurations can be modified to obtain a specific strength required for a specific application.

Thus since the invention disclosed herein may be embodied in other specific forms without departing from the spirit or general characteristics thereof, some of which forms have been indicated, the embodiments described herein are to be considered in all respects illustrative and not restrictive, by applying current or future knowledge. The scope of the invention is to be indicated by the appended claims, rather than by the foregoing description, and all changes which come within the meaning and range of equivalency of the claims are intended to be embraced therein.

What is claimed is:

1. A biphasic porous implantable device suitable for implantation in a living being, said porous implantable device comprising a high density porous zone and a low density porous zone, wherein said high density porous zone is created through a compression process applied to at least one part of a bioresorbable porous polymer material, wherein said compression process causes the sacrifice of at least some pores forming said high density porous zone, and wherein at least one part of said porous material is at least partially protected from compression thereby forming said low density porous zone.

2. The biphasic porous implantable device of claim 1, wherein said high density porous zone has further been subjected to a sintering or heating process, wherein said sintering or heating process causes pores of said high density porous zone to fuse together.

3. The biphasic porous implantable device of claim 1, wherein said sacrifice of said at least some pores creates laminar walls in said high-density porous zone.

4. The biphasic porous implantable device of claim 1, further comprising at least one additive component.

5. The biphasic porous implantable device of claim 4, wherein said at least one additive component is distributed in at least one manner selected from the group consisting of:
   a. uniformly throughout the porous implantable device;
   b. on the outside surfaces of said porous implantable device;
   c. within said pores of said porous material of said porous implantable device;
   d. between one or more of said porous material of said porous implantable device;

e. on the outside surfaces of the porous material of the porous implantable device; and f. in a portion of said porous implantable device.

6. The biphasic porous implantable device of claim 4, wherein said at least one additive is selected from the groups consisting of: a binder, a microstructure creating material, a reinforcing agent, a biologically active agent, a reinforcing material, and a tissue ingrowth promoting material.

7. The biphasic porous implantable device of claim 1, wherein said porous implant is arranged to be implanted as tissue reinforcement sheet.

8. The biphasic porous implantable device of claim 4, wherein the additive is selected from at least one of: screens, mesh, fibers, threads, rods, ceramic particles, glass particles, polymer particles, and metal particles.

9. The biphasic implantable device of claim 1 wherein said porous polymer material comprises a plurality of fibers.

10. The biphasic implantable device of claim 1, wherein said porous polymer material is non-fibrous.

11. The biphasic implantable device of claim 4 wherein said at least one additive component provides a depot within the implantable device, said depot being arranged to deliver said additive component over a period of time.

12. The biphasic implantable device of claim 1 wherein said bioresorbable porous polymer material comprises a plurality of resorbable layers.

13. A method of producing a high density, high strength porous matrix sheet containing low-density zones comprising:

a) providing a high porosity polymeric matrix sheet;

b) inducing glass-transition within said porous polymeric matrix sheet;

c) applying a compressive force within one or more dimensions using a plate containing shaped cavities, wherein the shaped cavities allow for less compression than the areas of the plate surrounding the cavities to achieve a new size or shape;

d) holding the porous polymer matrix sheet above glass transition at the new size and shape for a period of time allowing the molecular chains within the matrix sheet that are under compression to rotate or move to a lower energy state; and e) cooling the porous polymer to below the glass-transition wherein the polymer matrix sheet maintains the new size or shape.

\* \* \* \* \*